United States Patent
Kurihara et al.

(10) Patent No.: US 7,244,797 B2
(45) Date of Patent: *Jul. 17, 2007

(54) ORGANIC DOMAIN/INORGANIC DOMAIN COMPLEX MATERIALS AND USE THEREOF

(75) Inventors: Masaaki Kurihara, Numazu (JP); Hiroyoshi Matsuyama, Fuji (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 595 days.

This patent is subject to a terminal disclaimer.

(21) Appl. No.: 10/467,485

(22) PCT Filed: Feb. 8, 2002

(86) PCT No.: PCT/JP02/01103

§ 371 (c)(1),
(2), (4) Date: Aug. 8, 2003

(87) PCT Pub. No.: WO02/062872

PCT Pub. Date: Aug. 15, 2002

(65) Prior Publication Data

US 2004/0096421 A1 May 20, 2004

(30) Foreign Application Priority Data

Feb. 8, 2001 (JP) ............................. 2001-032444
Feb. 8, 2001 (JP) ............................. 2001-032452

(51) Int. Cl.
*C08F 30/04* (2006.01)
(52) U.S. Cl. .................. 526/241; 526/279; 424/400; 514/772; 514/772.3
(58) Field of Classification Search .............. None
See application file for complete search history.

(56) References Cited

U.S. PATENT DOCUMENTS 6,620,516 B1 * 9/2003 Kurihara et al. ............ 428/447

FOREIGN PATENT DOCUMENTS

WO   WO 00/34377   *   6/2000

OTHER PUBLICATIONS

Zhang et al. Journal of the American Chemical Society, 2001, 9204-9205.*

* cited by examiner

*Primary Examiner*—Michael P. Woodward
*Assistant Examiner*—Eric E. Silverman
(74) *Attorney, Agent, or Firm*—Birch, Stewart, Kolasch & Birch, LLP

(57) ABSTRACT

Disclosed are an organic domain/inorganic domain hybrid material comprising an organic domain comprising at least one water-soluble organic polymer having anionic and/or cationic functional groups, and an inorganic domain, the organic and inorganic domains being chemically bonded to each other through the functional groups, the inorganic domain comprising inorganic bridges, each independently comprising at least one Si atom, at least two O atoms and at least one divalent metal atom, wherein the Si atom and the O atoms together form at least one siloxane linkage arranged longitudinally of the inorganic bridge, wherein each divalent metal atom is ionically bonded to the O atoms of the siloxane linkages positioned adjacent to the divalent metal atoms, wherein, when at least a part of the organic domain is comprised of at least one organic polymer having an anionic functional group and optionally a cationic functional group, the organic domain/inorganic domain weight ratio is less than 1.0; and the use thereof as a hydrophilicity reagent and an antibacterial/antifungal reagent.

11 Claims, 3 Drawing Sheets

ORGANIC DOMAIN/INORGANIC DOMAIN COMPLEX MATERIALS AND USE THEREOF

This application is the national phase under 35 U.S.C. 371 of PCT International Application No. PCT/JP02/01103 which has an International filing date of Feb. 8, 2002, which designated the United States of America.

BACKGROUND OF THE INVENTION

1. Field of the Invention

The present invention relates to an organic domain/inorganic domain hybrid material and use thereof. More particularly, the present invention is concerned with an organic domain/inorganic domain hybrid material comprising: an organic domain comprising at least one water-soluble organic polymer having a plurality of functional groups, wherein each functional group is independently selected from the group consisting of an anionic functional group and a cationic functional group, and an inorganic domain. The organic domain and the inorganic domain are chemically bonded to each other through the functional groups of the organic polymer. The inorganic domain comprises a plurality of inorganic bridges having both ends thereof which are, respectively, chemically bonded to the functional groups of the organic polymer, wherein each inorganic bridge independently comprises at least one silicon atom, at least two oxygen atoms and at least one divalent metal atom, wherein the silicon atom(s) and the oxygen atoms together form at least one siloxane linkage which is arranged longitudinally of the inorganic bridge, wherein each divalent metal atom is ionically bonded to the oxygen atoms of the siloxane linkages positioned adjacent to the divalent metal atoms, wherein, when at least a part of the organic domain is comprised of at least one organic polymer having an anionic functional group and optionally a cationic functional group, the weight ratio of the organic domain to the inorganic domain is less than 1.0. The present invention is also concerned with a hydrophilicity reagent comprising the above-mentioned hybrid material; an antibacterial/antifungal reagent comprising the above-mentioned hybrid material; a hydrophilic coating composition comprising an aqueous dispersion (or emulsion) of an organic polymer and, dispersed therein, the above-mentioned hydrophilicity reagent; and a hydrophilic coating formed from the hydrophilic coating composition. The hybrid material of the present invention not only has many excellent functional properties (such as hydrophilicity and antibacterial property), which are ascribed to the component elements, component molecules, structure and the like of the hybrid material, but also can be easily produced. The hybrid material of the present invention is advantageous not only in that the hybrid material per se can be used as a functional material, but also in that the hybrid material can be used as a functional additive which is added to another organic or inorganic material so as to impart that material with hydrophilicity and/or antibacterial activity. Thus, the hybrid material is a commercially very valuable material.

2. Prior Art

Recently, vigorous studies have been made on hybrid materials each comprising a combination of at least two materials which are different in properties, because such hybrid materials exhibit excellent properties which cannot be obtained by a non-hybrid, single material. Among such hybrid materials, those comprising a combination of an organic polymeric material and an inorganic material have been attracting attention. Especially, with respect to the so-called "nano-composite material" (comprising a hybrid of an organic polymeric material and an inorganic material, in which the organic polymeric material or the inorganic material is present in the form of nanometer-size domains), such nano-composite material exhibits unique properties ascribed to its unique structure, and hence, the development of applications of the nano-composite material is expected.

As examples of widely known nano-composite materials, there can be mentioned a hybrid material obtained by uniformly dispersing a lamellar silicate (e.g., clay) as an inorganic material in a polyamide resin as an organic polymeric material (see A. Usuki et al., J. Mater. Res., 8, [5], 1179 (1993)), and a material composed of silica and an organic molecule (either of which is the main component), in which respective nano-size particles of silica and an organic molecule are mutually, finely dispersed, and which is produced by subjecting a silicon alkoxide as a raw material to sol-gel process in the presence of an organic molecule (oligomer or polymer) to form a silica (see Novak, M., Adv. Mater. 5,422 (1993) and Chujo, Y., and Encyclp. Poly. Sci. Tech., CRC Press, Boca Raton, 6, 4793 (1996)). These documents describe how to improve the mechanical properties of nano-composite materials or how to produce an intermediate of a porous silica. These documents do not however disclose a technique to produce a hybrid material exhibiting high hydrophilicity.

Therefore, studies have been made to produce a hybrid material having high hydrophilicity. For example, a hybrid material composed mainly of an inorganic material, in which a water-soluble polymer (such as polyacrylic acid or polymethacrylic acid) is intercalated between the layers of calcium silicate hydrate, has been developed (see H. Matsuyama et al., Chemistry of Materials, 11, 16–19 (1999)). With respect to this hybrid material, the use of calcium silicate hydrate which is a cement hydrate is an essential feature, and it has not been attempted to impart the hybrid material with various functions by using an inorganic material composed of essential elements other than those of a cement hydrate or by using a copolymer as an organic material. Further, there has been no document disclosing a technique to use the hybrid material as an additive to impart hydrophilicity to other materials.

On the other hand, a hydrophilized coating composition has been attracting attention as a coating composition having stain resistance wherein dirt on a coating formed from the coating composition can be easily washed away with water, such as rainwater, to prevent the dirt from adhering to the coating, and wherein occurrence of the so-called "raindrop dirt" (i.e., oily dirt adhering to the coating, which is formed along the path of flow of a raindrop) can be suppressed. Especially, in the field of aqueous coatings which have a low odor emission and are suitable for use at a construction site, it has been expected to develop a coating composition capable of forming a stain resistant coating, which can be used without cumbersome operations, such as a multiple coating operation and a mixing of liquid components of the coating composition at the construction site.

Recently, a number of coatings using a photocatalyst, such as titanium oxide, have been developed. However, when a photocatalyst is mixed with an organic substance, the organic substance is decomposed due to the oxidative activity of the photocatalyst. Therefore, when a photocatalyst is used in a coating composition, the photocatalyst needs to be used in combination with an inorganic material as a binder. Therefore, such a photocatalyst-containing coating composition is disadvantageous in that a coating formed from the composition is likely to suffer cracking, and that it becomes necessary to form a layer of an inorganic material on an undercoating for the photocatalyst-containing coating composition. Thus, the use of the photocatalyst-containing coating composition for coating an outer wall has serious problems from the viewpoint of workability and cost.

With respect to a technique to hydrophilize a coating composition by using a hybrid material, Unexamined Japanese Patent Application Laid-Open Specification No. 2000-264971 discloses a technique to modify the surface of a polymer in a polymer emulsion with an organosilicon compound; however, this technique has a problem that the production of the coating composition becomes complicated. Further, WO99/05228 discloses a technique in which a silicon alkoxide is mixed as a hydrophilicity reagent with a polymer emulsion to obtain a hydrophilic coating composition which can be used for forming a stain resistant coating. However, alkoxides undego hydrolysis when contacted with water, so that the hydrophilic coating composition has a disadvantageously short pot life (less than one day). Therefore, the use of such a hydrophilic coating is difficult from a practical point of view.

Further, Unexamined Japanese Patent Application Laid-Open Specification No. Hei 9-227118 (corresponding to U.S. Pat. No. 5,786,417) discloses a method using a method in which an organic clay composite (comprising clay layers and polyalkylene oxide position between and bonded to the clay layers) is used as a thickner for an aqueous coating composition. However, a coating obtained by this technique is not hydrophilized and does not have stain resistance.

As a material having an antibacterial property, there is known an inorganic material-containing antibacterial reagent using a metal (e.g., silver or copper) having an antibacterial property or a sterilizing organic compound having a specific chemical structure.

For example, Unexamined Japanese Patent Application Laid-Open Specification No. Hei 9-30915 discloses a sintered material obtained by calcining a material comprising a silica gel (as a substrate) having carried thereon an antibacterial metal, such as silver or copper. However, this method involves a complicated operation for calcination, and hence, the productivity of the desired material is not satisfactorily high. In addition, the amount of the antibacterial metal which can be contained in the material is only several % by weight.

Further, Unexamined Japanese Patent Application Laid-Open Specification No. Hei 10-130105 (corresponding to U.S. Pat. No. 5,876,738) discloses a method for obtaining a lamellar silicate (carrier) having an organic antifungal material supported between the layers of the lamellar silicate. However, the resultant product in which the organic substance is simply supported between the layers of the lamellar silicate cannot maintain the desired effect for a satisfactorily long period of time.

Further, recently, materials using a photocatalyst have been widely studied. For example, Unexamined Japanese Patent Application Laid-Open Specification No. 2000-17356 (corresponding to U.S. Pat. No. 6,313,064) discloses a photocatalyst alloy comprising copper and titanium. However, a photocatalyst is effective only at a location (such as near a bright window) exposed to direct sunlight, and cannot exhibit a satisfactory effect in so-called wet areas (such as a bath room and a kitchen) due to lack of light.

Thus, there has not been proposed an excellent organic/inorganic hybrid material which has various functional properties, such as hydrophilicity and antibacterial property, which can be easily produced and used.

SUMMARY OF THE INVENTION

In this situation, the present inventors have made extensive and intensive studies with a view toward solving the above-mentioned problems accompanying the prior art. As a result, it has unexpectedly been found that an organic domain/inorganic domain hybrid material having a specific structure is advantageous not only in that the hybrid material per se can be used as a functional material, but also in that the hybrid material can be used as a functional additive which is added to another organic or inorganic material so as to impart that material with hydrophilicity and/or antibacterial activity, so that the hybrid material is a commercially very valuable material. The above-mentioned organic domain/inorganic domain hybrid material comprises: an organic domain comprising at least one water-soluble organic polymer having a plurality of functional groups, wherein each functional group is independently selected from the group consisting of an anionic functional group and a cationic functional group, and an inorganic domain. The organic domain and the inorganic domain are chemically bonded to each other through the functional groups of the organic polymer, the inorganic domain comprising a plurality of inorganic bridges having both ends thereof which are, respectively, chemically bonded to the functional groups of the organic polymer, wherein each inorganic bridge independently comprises at least one silicon atom, at least two oxygen atoms and at least one divalent metal atom, wherein the silicon atom(s) and the oxygen atoms together form at least one siloxane linkage which is arranged longitudinally of the inorganic bridge, wherein each divalent metal atom is ionically bonded to the oxygen atoms of the siloxane linkages positioned adjacent to the divalent metal atoms, wherein, when at least a part of the organic domain is comprised of at least one organic polymer having an anionic functional group and optionally a cationic functional group, the weight ratio of the organic domain to the inorganic domain is less than 1.0. Based on this finding, the present invention has been completed.

Accordingly, it is an object of the present invention to provide an excellent organic domain/inorganic domain hybrid material which not only has various functional properties, such as hydrophilicity and antibacterial property, but also can be easily produced.

It is another object of the present invention to provide a hydrophilicity reagent comprising the above-mentioned hybrid material, which can be used to form a coating which improves characteristics of the surfaces (e.g., a resin surface and a coated surface) of various articles (for example, the hydrophilicity agent can be used to make it easy to wash away dirt attached to a resin surface or a coated surface with water, or to prevent a resin surface or a coated surface from getting tarnished by the adhesion of very small waterdrops, or to prevent a scattering of the light caused by waterdrops on a resin surface or a coated surface.

It is still another object of the present invention to provide a hydrophilic coating composition comprising an aqueous dispersion of an organic polymer and, dispersed therein, the above mentioned hydrophilicity reagent, which coating composition does not require cumbersome operations, such as a double coating operation and a mixing of the liquid components of the coating composition at the time of the use of the coating composition, thus exhibiting excellent workability, and to provide a hydrophilic coating formed from the hydrophilic coating composition.

It is a further object of the present invention to provide an antibacterial/antifungal reagent comprising the above-mentioned hybrid material.

The foregoing and other objects, features and advantages of the present invention will be apparent from the following detailed description and appended claims taken in connection with the accompanying drawing.

BRIEF DESCRIPTION OF THE DRAWINGS

In the drawings:

In FIGS. 1 through 3, M denotes a divalent metal atom.

DETAILED DESCRIPTION OF THE INVENTION

Figure 1:
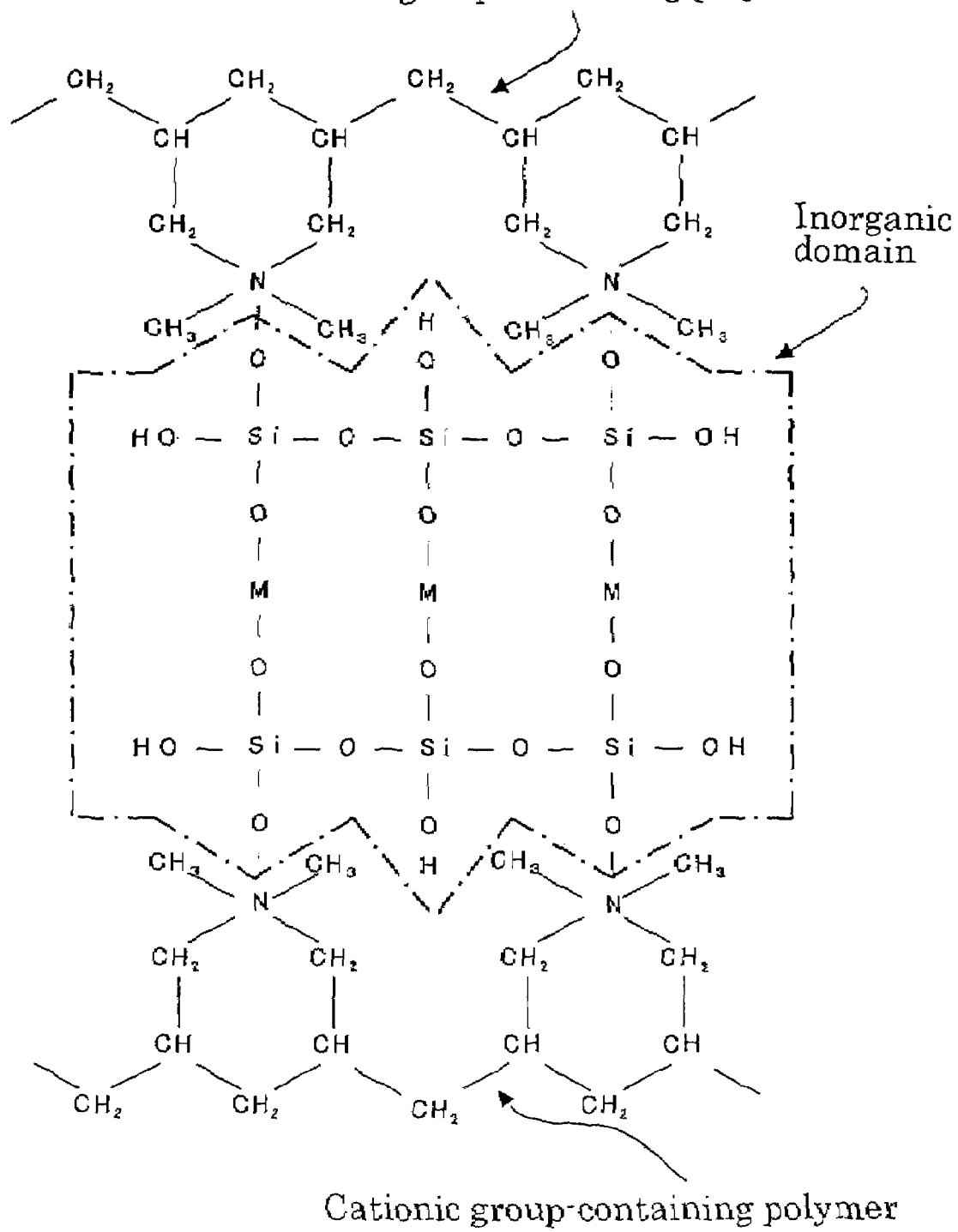
FIG. 1 is an explanatory diagram showing the structure of one embodiment of the organic domain/inorganic domain hybrid material of the present invention, in which each end of an inorganic bridge is bonded to a cationic functional group of an organic polymer.

In one aspect of the present invention, there is provided an organic domain/inorganic domain hybrid material comprising:

an organic domain comprising at least one water-soluble organic polymer having a plurality of functional groups, wherein each functional group is independently selected from the group consisting of an anionic functional group and a cationic functional group, and an inorganic domain, the organic domain and the inorganic domain being chemically bonded to each other through the functional groups of the organic polymer, the inorganic domain comprising a plurality of inorganic bridges having both ends thereof which are, respectively, chemically bonded to the functional groups of the organic polymer, wherein each inorganic bridge is independently represented by the formula (1):

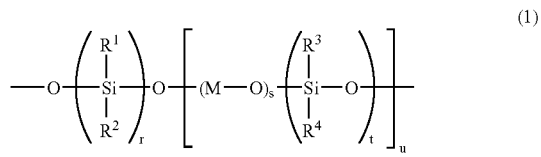

(1)

wherein each M independently represents a divalent metal atom selected from the group consisting of beryllium, magnesium, calcium, strontium, barium, copper, zinc, nickel, iron, manganese, chromium and cobalt, and each of $R^1$ to $R^4$ independently represents a hydrogen atom, a hydroxyl group, a monovalent organic group, a monovalent, siloxane linkage-containing group, or a single bond which is linked to any one of $R^1$ to $R^4$ of an adjacent inorganic bridge through at least an oxygen atom, wherein each of r, s and t is independently an integer of 1 or more, and u is an integer of 0 or more, provided that, when both ends of the inorganic bridge are, respectively, bonded to cationic functional groups, u is an integer of 1 or more, and wherein, when at least one end of the inorganic bridge is bonded to an anionic functional group, the bonding is made through a divalent metal atom selected from the group consisting of beryllium, magnesium, calcium, strontium, barium, copper, zinc, nickel, iron, manganese, chromium and cobalt, wherein, when at least a part of the organic domain is comprised of at least one organic polymer having an anionic functional group and optionally a cationic functional group, the weight ratio of the organic domain to the inorganic domain is less than 1.0, and wherein, when at least a part of the organic domain is comprised of at least one organic polymer having an anionic functional group and optionally a cationic functional group, or when the organic domain is comprised of at least one organic polymer having a cationic functional group and having no anionic functional group and when the weight ratio of the organic domain to the inorganic domain is less than 1.0, not all divalent metal atoms of the inorganic domain are simultaneously calcium atoms.

In another aspect of the present invention, there is provided a hydrophilicity reagent comprising the above-mentioned organic domain/inorganic domain hybrid material. In the hydrophilicity reagent of the present invention, all of divalent metal atoms of the inorganic domain can be simultaneously calcium atoms.

In still another aspect of the present invention, there is provided a hydrophilic coating composition comprising an aqueous dispersion of an organic polymer and, dispersed therein, the above mentioned hydrophilicity reagent.

In a further aspect of the present invention, there is provided a hydrophilic coating formed from the above-mentioned hydrophilic coating composition.

In still a further aspect of the present invention, there is provided an antibacterial/antifungal reagent comprising the above-mentioned organic domain/inorganic domain hybrid material. In the antibacterial/antifungal reagent of the present invention, all divalent metal atoms of the inorganic domain can be simultaneously calcium atoms.

For easy understanding of the present invention, the essential features and various preferred embodiments of the present invention are enumerated below.

1. An organic domain/inorganic domain hybrid material comprising:

an organic domain comprising at least one water-soluble organic polymer having a plurality of functional groups, wherein each functional group is independently selected from the group consisting of an anionic functional group and a cationic functional group, and an inorganic domain, the organic domain and the inorganic domain being chemically bonded to each other through the functional groups of the organic polymer, the inorganic domain comprising a plurality of inorganic bridges having both ends thereof which are, respectively, chemically bonded to the functional groups of the organic polymer, wherein each inorganic bridge is independently represented by the formula (1):

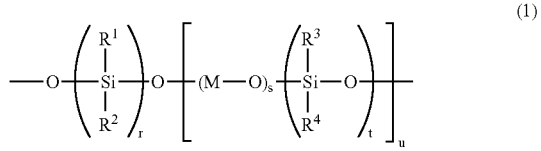

wherein each M independently represents a divalent metal atom selected from the group consisting of beryllium, magnesium, calcium, strontium, barium, copper, zinc, nickel, iron, manganese, chromium and cobalt, and each of $R^1$ to $R^4$ independently represents a hydrogen atom, a hydroxyl group, a monovalent organic group, a monovalent, siloxane linkage-containing group, or a single bond which is linked to any one of $R^1$ to $R^4$ of an adjacent inorganic bridge through at least an oxygen atom, wherein each of r, s and t is independently an integer of 1 or more, and u is an integer of 0 or more, provided that, when both ends of the inorganic bridge are, respectively, bonded to cationic functional groups, u is an integer of 1 or more, and wherein, when at least one end of the inorganic bridge is bonded to an anionic functional group, the bonding is made through a divalent metal atom selected from the group consisting of beryllium, magnesium, calcium, strontium, barium, copper, zinc, nickel, iron, manganese, chromium and cobalt, wherein, when at least a part of the organic domain is comprised of at least one organic polymer having an anionic functional group and optionally a cationic functional group, the weight ratio of the organic domain to the inorganic domain is less than 1.0, and wherein, when at least a part of the organic domain is comprised of at least one organic polymer having an anionic functional group and optionally a cationic functional group, or when the organic domain is comprised of at least one organic polymer having a cationic functional group and having no anionic functional group and when the weight ratio of the organic domain to the inorganic domain is less than 1.0, not all divalent metal atoms of the inorganic domain are simultaneously calcium atoms.

2. The hybrid material according to item 1, wherein the organic polymer is selected from the group consisting of:
   an organic polymer having a plurality of cationic functional groups,
   an organic polymer having a plurality of anionic functional groups and a plurality of cationic functional groups, and
   a mixture of an organic polymer having a plurality of anionic functional groups and an organic polymer having a plurality of cationic functional groups.

3. The hybrid material according to item 1 or 2, wherein at least a part of the divalent metal atoms of the inorganic domain is comprised of a magnesium atom, and the inorganic domain is amorphous.

4. The hybrid material according to any one of items 1 to 3, which is produced by a process comprising contacting, in the presence of an aqueous medium and at a pH of 7 or more, the following chemical species (a), (b) and (c) with one another:
   (a) silicate anions formed from a silicate compound or a silicon halide,
   (b) polymer ions formed from at least one water-soluble organic polymer having a plurality of functional groups, wherein each functional group is independently selected from the group consisting of an anionic functional group and a cationic functional group, and
   (c) divalent metal cations formed from a salt of at least one divalent metal selected from the group consisting of beryllium, magnesium, calcium, strontium, barium, copper, zinc, nickel, iron, manganese, chromium and cobalt, provided that, when at least a part of the organic domain is comprised of at least one organic polymer having an anionic functional group and optionally a cationic functional group, or when the organic domain is comprised of at least one organic polymer having a cationic functional group and having no anionic functional group and when the weight ratio of the organic domain to the inorganic domain is less than 1.0, not all divalent metal cations are simultaneously calcium cations.

5. A hydrophilicity reagent comprising an organic domain/inorganic domain hybrid material comprising:
   an organic domain comprising at least one water-soluble organic polymer having a plurality of functional groups, wherein each functional group is independently selected from the group consisting of an anionic functional group and a cationic functional group, and
   an inorganic domain,
   the organic domain and the inorganic domain being chemically bonded to each other through the functional groups of the organic polymer,
   the inorganic domain comprising a plurality of inorganic bridges having both ends thereof which are, respectively, chemically bonded to the functional groups of the organic polymer, wherein each inorganic bridge is independently represented by the formula (1):

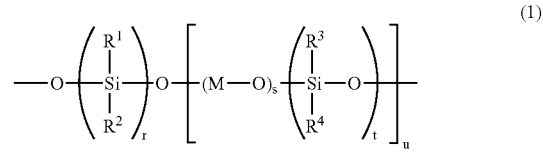

wherein each M independently represents a divalent metal atom selected from the group consisting of beryllium, magnesium, calcium, strontium, barium, copper, zinc, nickel, iron, manganese, chromium and cobalt, and each of $R^1$ to $R^4$ independently represents a hydrogen atom, a hydroxyl group, a monovalent organic group, a monovalent, siloxane linkage-containing group, or a single bond which is linked to any one of $R^1$ to $R^4$ of an adjacent inorganic bridge through at least an oxygen atom, wherein each of r, s and t is independently an integer of 1 or more, and u is an integer of 0 or more, provided that, when both ends of the inorganic bridge are, respectively, bonded to cationic functional groups, u is an integer of 1 or more, and wherein, when at least one end of the inorganic bridge is bonded to an anionic functional group, the bonding is made through a divalent metal atom selected from the group consisting of beryllium, magnesium, calcium, strontium, barium, copper, zinc, nickel, iron, manganese, chromium and cobalt, wherein, when at least a part of the organic domain is comprised of at least one organic polymer having an anionic functional group and optionally a cationic functional group, the weight ratio of the organic domain to the inorganic domain is less than 1.0.

6. The hydrophilicity reagent according to item 5, wherein the hybrid material is produced by a process comprising contacting, in the presence of an aqueous medium and at a pH of 7 or more, the following chemical species (a), (b) and (c) with one another:

(a) silicate anions formed from a silicate compound or a silicon halide, (b) polymer ions formed from at least one water-soluble organic polymer having a plurality of functional groups, wherein each functional group is independently selected from the group consisting of an anionic functional group and a cationic functional group, and (c) divalent metal cations formed from a salt of at least one divalent metal selected from the group consisting of beryllium, magnesium, calcium, strontium, barium, copper, zinc, nickel, iron, manganese, chromium and cobalt.

7. A hydrophilic coating composition comprising an aqueous dispersion of an organic polymer and, dispersed therein, the hydrophilicity reagent of item 5 or 6.

8. A hydrophilic coating formed from the hydrophilic coating composition of item 7.

9. An antibacterial/antifungal reagent comprising an organic domain/inorganic domain hybrid material comprising:

an organic domain comprising at least one water-soluble organic polymer having a plurality of functional groups, wherein each functional group is independently selected from the group consisting of an anionic functional group and a cationic functional group, provided that at least a part of the organic polymer is comprised of at least one organic polymer having a cationic functional group and optionally an anionic functional group, and an inorganic domain, the organic domain and the inorganic domain being chemically bonded to each other through the functional groups of the organic polymer, the inorganic domain comprising a plurality of inorganic bridges having both ends thereof which are, respectively, chemically bonded to the functional groups of the organic polymer, wherein each inorganic bridge is independently represented by the formula (1):

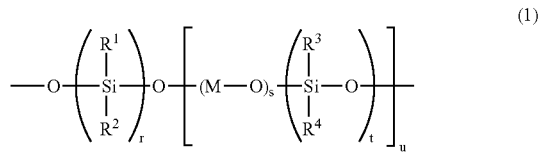

(1)

wherein each M independently represents a divalent metal atom selected from the group consisting of beryllium, magnesium, calcium, strontium, barium, copper, zinc, nickel, iron, manganese, chromium and cobalt, and each of $R^1$ to $R^4$ independently represents a hydrogen atom, a hydroxyl group, a monovalent organic group, a monovalent, siloxane linkage-containing group, or a single bond which is linked to any one of $R^1$ to $R^4$ of an adjacent inorganic bridge through at least an oxygen atom, wherein each of r, s and t is independently an integer of 1 or more, and u is an integer of 0 or more, provided that, when both ends of the inorganic bridge are, respectively, bonded to cationic functional groups, u is an integer of 1 or more, and wherein, when at least one end of the inorganic bridge is bonded to an anionic functional group, the bonding is made through a divalent metal atom selected from the group consisting of beryllium, magnesium, calcium, strontium, barium, copper, zinc, nickel, iron, manganese, chromium and cobalt, wherein, when a part of the organic domain is comprised of at least one organic polymer having an anionic functional group and optionally a cationic functional group, the weight ratio of the organic domain to the inorganic domain is less than 1.0.

10. The antibacterial/antifungal reagent according to item 9, wherein the divalent metal atoms of the inorganic domain are comprised of at least one divalent metal atom selected from the group consisting of copper, zinc, nickel, iron, manganese, chromium and cobalt.

11. The antibacterial/antifungal reagent according to item 9 or 10, wherein the hybrid material is produced by a process comprising contacting, in the presence of an aqueous medium and at a pH of 7 or more, the following chemical species (a), (b) and (c) with one another:

(a) silicate anions formed from a silicate compound or a silicon halide, (b) polymer ions formed from at least one water-soluble organic polymer having a plurality of functional groups, wherein each functional group is independently selected from the group consisting of an anionic functional group and a cationic functional group, provided that at least a part of the organic polymer is comprised of at least one organic polymer having a cationic functional group and optionally an anionic functional group, and (c) divalent metal cations formed from a salt of at least one divalent metal selected from the group consisting of beryllium, magnesium, calcium, strontium, barium, copper, zinc, nickel, iron, manganese, chromium and cobalt.

Hereinbelow, the present invention is described in detail.

The organic domain/inorganic domain hybrid material of the present invention comprises: an organic domain comprising at least one water-soluble organic polymer having a plurality of functional groups, wherein each functional group is independently selected from the group consisting of an anionic functional group and a cationic functional group; and an inorganic domain. The organic domain and the inorganic domain are chemically (ionically) bonded to each other through the functional groups of the organic polymer.

As the organic polymer used in the organic domain, it is preferred to use at least one organic polymer selected from the group consisting of:

at least one organic polymer having an anionic functional group and optionally a cationic functional group, at least one organic polymer having an cationic functional group and optionally an anionic functional group, at least one organic polymer having an anionic functional group and a cationic functional group, or a mixture of at least one organic polymer having an anionic functional group and at least one organic polymer having a cationic functional group.

In the case of an antibacterial/antifungal reagent comprising the hybrid material of the present invention, at least a part of the organic polymer comprises at least one organic polymer having a cationic functional group and optionally an anionic functional group. With respect to such an organic polymer, there is no particular limitation so long as the organic polymer has a cationic functional group; however, as specific examples of preferred organic polymers, there can be mentioned an organic polymer having a plurality of cationic functional groups, an organic polymer having a plurality of anionic functional groups and a plurality of cationic functional groups, and a mixture of an organic polymer having a plurality of anionic functional groups and an organic polymer having a plurality of cationic functional groups. The antibacterial/antifungal reagent of the present invention exhibits a killing effect or a proliferation suppressing effect with respect to at least one microbe selected from the group consisting of bacteria and fungi.

The water-soluble organic polymer used in the hybrid material of the present invention is a polymer which exhibits a solubility of 1% by weight or more in a water-containing solvent which has a water content of 50% by weight or more at room temperature. With respect to the conditions under which the organic polymer is dissolved in the water-containing solvent, there is no particular limitation so long as the organic polymer exhibits the above-mentioned solubility. For example, a polyvinyl alcohol gets dissolved in water only at high temperatures; however, once the polyvinyl alcohol gets dissolved in water at a high temperature, the polyvinyl alcohol remains dissolved in water even after the temperature is lowered to room temperature. Therefore, in the present invention, the polyvinyl alcohol is regarded as an organic polymer which exhibits the above-mentioned solubility, and hence, can be used as the water-soluble organic polymer.

With respect to the water-containing solvent mentioned above, there is no particular limitation so long as the solvent has a water content of 50% by weight at room temperature. When the solvent is in the form of a mixed solvent of water and another substance, the substance needs to be completely dissolved in water. Examples of substances which can be used in the mixed solvent include water-soluble solvents, such as alcohols, ketones, esters, dimethylformamide and dimethylsulfoxide; inorganic or organic acids, such as hydrochloric acid, sulfuric acid, acetic acid and p-toluenesulfonic acid; inorganic or organic salts, such as sodium chloride and sodium acetate; alkaline substances, such as an alkali metal hydroxide, ammonia and an amine; and surfactants, such as a nonionic surfactant, an anionic surfactant, a cationic surfactant and a silicone-containing surfactant.

The organic polymer used in the production of the hybrid material of the present invention has at least one hydrophilic functional group in terms of an average number of the functional group per polymer chain of the organic polymer. The organic polymer may contain a polymer chain having no functional group; however, it is preferred that each polymer chain has at least one functional group.

In the present invention, the "anionic functional group" means a functional group which dissociates to form an anion in an aqueous medium, and the "cationic functional group" means a functional group which dissociates to form a cation in an aqueous medium. Preferred examples of anionic functional groups include a carboxylic acid group and salts thereof, a sulfonic acid group and salts thereof, a phosphoric acid group and salts thereof, a hydroxyl group, and a mixture thereof. Preferred examples of cationic functional groups include quaternary salts of a nitrogen-containing heterocyclic compound, such as pyridine or imidazole, and quaternary ammonium salts. When the organic domain (composed of an organic polymer) of the hybrid material of the present invention has an anionic functional group (i.e., a functional group which dissociates to form an anion), the organic domain is bonded to the siloxane linkage (present in the inorganic domain) through a divalent metal atom, to thereby combine the organic and inorganic domains to form a hybrid material. On the other hand, when the organic domain has a cationic functional group (i.e., a functional group which dissociates to form a cation), the organic domain is directly bonded to the siloxane linkage, to thereby form a hybrid material. Thus, in the hybrid material of the present invention, the organic and inorganic domains are chemically bonded to each other. Such a hybrid material of the present invention is an excellent material which is advantageous not only in that the material has both of the advantageous features of the organic domain and the advantageous features of the inorganic domain, wherein properties deficient in one of the two types of the domains may be compensated by the other domain, but also in that, when the hybrid material is incorporated as an additive into a matrix comprising an organic or inorganic material, the hybrid material exhibits excellent compatibility with the matrix, so that it is possible to obtain an excellent product (comprising the matrix and the hybrid material) which simultaneously exhibits opposite properties (such as hydrophilicity and water resistance). As the above-mentioned functional group of the organic polymer, it is preferred to use an anionic functional group selected from the group consisting of a carboxylic acid group and salts thereof, a sulfonic acid group and salts thereof and a phosphoric acid group and salts thereof, and/or a cationic functional group, such as a quaternary salt of nitrogen-containing heterocyclic compounds or a quaternary ammonium salt, because the organic domain and the inorganic domain can be strongly bonded to each other. Among these functional groups, from the viewpoint of ease in combining the organic and inorganic domains to form a hybrid material, it is more preferred to use a carboxylic acid group or a salt thereof as the anionic functional group and/or a quaternary salt of a nitrogen-containing hetrocyclic compound or a quaternary ammonium salt as the cationic functional group. When the hybrid material is used as a hydrophilicity reagent, it is preferred that a plurality of the above-mentioned preferred functional groups are contained in a polymer chain of the organic polymer, and it is more preferred that the number of the above-mentioned preferred functional groups contained in the organic polymer is 5 or more in terms of an average number of the functional groups per polymer chain of the organic polymer. Further, it is preferred that 10 mol % or more of the monomer units constituting the organic polymer have any of the above-mentioned preferred functional groups, and that 50 mol % or more of all hydrophilic functional groups present in the polymer chain are the above-mentioned preferred functional groups. Specifically, the presence of such a large amount of the above-mentioned preferred functional groups is advantageous for the following reason. In the present invention, the functional groups of the organic polymer not only form linkages between the organic domain and the inorganic domain, but also improve the hydrophilicity of the resultant hybrid material. The above-mentioned preferred functional groups have high hydrophilicity as compared to other functional groups, so that the organic polymer containing a large amount of the above-mentioned preferred functional group(s) exhibits favorable hydrophilization effect. On the other hand, when the hybrid material is used as an antibacterial/antifungal reagent, it is preferred to use cationic functional groups, because a polymer having cationic functional groups exhibits antibacterial property, thereby improving the antibacterial property of the hybrid material.

The presence of the functional groups of the organic polymer can be confirmed by organochemical spectroscopy, such as infrared spectroscopy or nuclear magnetic resonance method (NMR method), or fluorescence X ray spectroscopy.

The ratio of different functional groups can be determined by the above-mentioned methods using a calibration curve prepared for the determination.

Examples of organic polymers having an anionic functional group which can be used in the present invention include homopolymers and copolymers, each independently produced by polymerizing at least one anionic functional group-containing monomer selected from the group consisting of vinyl alcohol, 2-hydroxyethyl (meth)acrylate, 2-hydroxypropyl (meth)acrylate, 2-hydroxybutyl (meth)acrylate, glycerol mono(meth)acrylate, and (meth)acrylic acid and salts (an alkali metal salt and an ammonium salt) thereof, itaconic acid and salts (an alkali metal salt and an ammonium salt) thereof, 2-(meth)acryloyloxyethylsuccinic acid and salts (an alkali metal salt and an ammonium salt) thereof, 2-(meth)acryloyloxyethylphthalic acid and salts (an alkali metal salt and an ammonium salt) thereof, 2-(meth)acryloyloxyethylhexahydrophthalic acid and salts (an alkali metal salt and an ammonium salt) thereof, 2-(meth)acrylamide-2-methylpropanesulfonic acid and salts thereof, styrenesulfonic acid and salts thereof, vinylsulfonic acid and salts thereof, 2-sulfoethyl (meth)acrylate and salts thereof, and 2-(meth)acryloyloxyethylphosphoric acid and salts thereof. Further examples of organic polymers having an anionic functional group include copolymers, each independently produced by copolymerizing at least one of the above-mentioned anionic functional group-containing monomers with at least one comonomer selected from the group consisting of (meth)acrylamide, (meth)acryloyl-morpholine, vinylpyridine, N-methyl(meth)acrylamide, N,N'-dimethyl (meth)acrylamide, N,N'-dimethylaminopropyl(meth)acrylamide, N,N'-dimethylaminoethyl (meth)acrylate, N,N'-diethylaminoethyl (meth)acrylate, N,N'-dimethylaminoneopentyl (meth)acrylate, N-vinyl-2-pyrrolidone, diacetonacrylamide, N-methylol(meth) acrylamide, methoxytriethylene glycol (meth)acrylate, methoxytetraethylene glycol (meth)acrylate, methoxypolyethylene glycol (meth)acrylate, butoxyethyl (meth)acrylate, phenoxyethyl (meth)acrylate, phenoxydiethylene glycol (meth)acrylate, phenoxyethylene glycol (meth)acrylate, phenoxypolyethylene glycol (meth)acrylate, nonylphenoxyethyl (meth)acrylate, isobornyl (meth)acrylate, lauryl (meth) acyrlate, tridecyl (meth)acrylate, stearyl (meth)acrylate, isodecyl (meth)acrylate, cyclohexyl (meth)acrylate, tetrafurfuryl (meth)acrylate, benzyl (meth)acrylate, methyl (meth)acryalte, ethyl (meth)acryalte and styrene. Each of the above-exemplified polymers needs to exhibit the above-mentioned water solubility.

As the organic polymer having a cationic functional group, it is preferred to use an organic polymer having a cationic functional group, such as a quaternary salt of a nitrogen-containing heterocyclic compound (e.g., pyridine or imidazole) or a quaternary ammonium salt. Examples of such organic polymers include homopolymers and copolymers, each independently produced by polymerizing at least one cationic functional group-containing monomers selected from the group consisting of a quaternized product of dimethylaminoethyl (meth)acrylate, diallyldimethylammonium chloride, 4-vinylbenzyltrimethylammonium chloride and 4-vinyl-1-methylpyridinium bromide; and copolymers, each independently produced by copolymerizing at least one of the above-mentioned cationic functional group-containing monomers with at least one monomer selected from the above-mentioned anionic functional group-containing monomers which can be used in the production of the organic polymers having an anionic functional group. These polymers need to exhibit the above-mentioned water solubility.

In the polymerization of these monomers, the anionic functional group-containing monomer and the cationic functional group-containing monomer can be used in combination; however, in this case, a precipitation may occur due to the ionic interaction between the functional groups of the monomers, and hence, the polymerization conditions should be strictly controlled.

Also, when a polymer having an anionic functional group and a polymer having a cationic functional group are used in combination, the polymers may become insoluble due to the ionic interaction of the functional groups of the polymers, and hence, care must be taken with respect to the order of addition of the polymers at the time of formation of the hybrid material and the like, so as not to hinder the formation of the hybrid material.

Further, when an anionic functional group-containing monomer and a cationic functional group-containing monomer are used in combination, or when a polymer having an anionic functional group and a polymer having a cationic functional group are used in combination, the preferred combination of the functional groups is a combination of at least one anionic functional group selected from the group consisting of a sulfonic acid group and salts thereof, and a phosphoric acid group and salts thereof, with at least one cationic functional group selected from the group consisting of quaternary salts of nitrogen-containing heterocyclic compounds and quaternary ammonium salts.

Polymers other than exemplified above can also be used so long as the polymers exhibit the above-mentioned solubility and have the above-mentioned functional groups. Examples of such polymers include polysaccharides, such as salts of alginic acid and derivatives thereof, and cellulose and derivatives thereof; modified polysaccharides, such as an iodide of methyl glycol chitosan; natural polymers, such as gum arabic and gelatin; polyvinyl alcohol, a partially saponified product thereof and a modified product thereof; polymers to which functional groups are introduced after the polymerization (such as a partially hydrolyzed product of polyacrylamide); polymers (such as a homopolymer or copolymer of glycidol) obtained by cationic polymerization; polymers (such as a condensation product of an alkali metal salt of naphthalene sulfonate with formaldehyde) obtained by condensation reaction; polyurethane, polyurea, polyamide and the like which have been rendered water-soluble by introduction of functional groups.

Further, in the case of the hybrid material of the present invention which is for a specific use, such as an antibacterial/antifungal reagent, the organic polymer used in the organic domain may be a polymer which has, in a main chain or side chain thereof, a haloalkylthio type functional group having antibacterial property and/or antifungal property, or a polymer which has, in a main chain or side chain thereof, an azole derivative (as a functional group) having antibacterial property and/or antifungal property, each of which is synthesized by copolymerization conducted in such a manner that the above-mentioned anionic or cationic functional groups used to form linkages with the inorganic domain are introduced to the polymer.

Further, in the present invention, the weight average molecular weight of the water-soluble organic polymer is preferably 1,000 or more. When the weight average molecular weight of the polymer is less than 1,000, the effects achieved by the hybrid material are sometimes lowered depending on the structure of the hybrid material. The weight average molecular weight of the water-soluble organic polymer is more preferably 5,000 or more, still more preferably 10,000 or more. In the present invention, the weight average molecular weight is measured by gel permeation chromatography (GPC) using a modified calibration curve therefor, which is obtained by modifying a calibration curve obtained with respect to standard monodisperse polyethyrene glycol samples. When the molecular weight of the polymer is very high, e.g., 10,000,000 or more, it is sometimes difficult to measure the molecular weight by the above-mentioned method; however, of course, a polymer having such a high molecular weight can also be used in the present invention. Further, with respect to the weight average molecular weight of the water-soluble organic polymer, there is no particular upper limit, and the weight average molecular weight is appropriately selected in view of the relationship between the concentration and viscosity of a reaction mixture during the production of the hybrid material and the desired properties of the hybrid material.

When a hydrophilic coating composition is produced by using the hybrid material of the present invention as a hydrophilicity reagent, the average molecular weight of the water-soluble organic polymer used in the hybrid material is preferably 1,000,000 or less, more preferably 500,000 or less, still more preferably 200,000 or less, from the viewpoint of ease in handing of the polymer. Further, when the water-soluble organic polymer having an anionic functional group is used, the organic domain/inorganic domain weight ratio may become 1.0 or more (depending on the mixing ratio of the polymer to the component materials of the inorganic domain), so that the resultant hybrid material exhibits substantially no fluidity. This causes problems such that it becomes difficult to disperse the hydrophilicity agent (comprising the hybrid material) uniformly in the aqueous dispersion of an organic polymer used in the production of the hydrophilic coating composition. In such a case, it is preferred to use an anionic functional group-containing polymer having a weight average molecular weight of 100,000 or less.

The inorganic domain of the hybrid material of the present invention comprises a plurality of inorganic bridges having both ends thereof which are, respectively, chemically bonded to the functional groups of the organic polymer, wherein each inorganic bridge is independently represented by the formula (1):

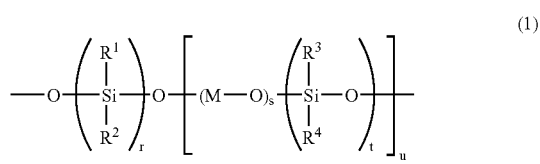

(1)

wherein each M independently represents a divalent metal atom selected from the group consisting of beryllium, magnesium, calcium, strontium, barium, copper, zinc, nickel, iron, manganese, chromium and cobalt, and each of $R^1$ to $R^4$ independently represents a hydrogen atom, a hydroxyl group, a monovalent organic group, a monovalent, siloxane linkage-containing group, or a single bond which is linked to any one of $R^1$ to $R^4$ of an adjacent inorganic bridge through at least an oxygen atom, wherein each of r, s and t is independently an integer of 1 or more, and u is an integer of 0 or more, provided that, when both ends of the inorganic bridge are, respectively, bonded to cationic functional groups, u is an integer of 1 or more, and wherein, when at least one end of the inorganic bridge is bonded to an anionic functional group, the bonding is made through a divalent metal atom selected from the group consisting of beryllium, magnesium, calcium, strontium, barium, copper, zinc, nickel, iron, manganese, chromium and cobalt.

As mentioned above, when at least a part of the organic domain is comprised of at least one organic polymer having an anionic functional group and optionally a cationic functional group, or when the organic domain is comprised of at least one organic polymer having a cationic functional group and having no anionic functional group and when the weight ratio of the organic domain to the inorganic domain is less than 1.0, not all divalent metal atoms of the inorganic domain are simultaneously calcium atoms. Further, in one aspect of the hybrid material of the present invention, it is a prerequisite that not all divalent metal atoms of the inorganic domain should be simultaneously calcium atoms.

When the hybrid material of the present invention is used as a hydrophilicity reagent or an antibacterial/antifungal reagent, all of divalent metal atoms of the inorganic domain may simultaneously be calcium atoms.

As a representative example of the structure of the inorganic bridge represented by formula (1) above, there can be mentioned a structure in which r=1 and u=0; a structure in which all of r, s, t and u are 1; and a structure in which r=1 and the s/t ratio=1/1.

When the hybrid material of the present invention is used as a material (such as a hydrophilicity reagent) which is desired to exhibit high hydrophilicity, for the purpose of achieving such high hydrophilicity, it is preferred that each of $R^1$ to $R^4$ in formula (1) above independently represents a hydroxyl group, a monovalent, siloxane linkage-containing group, or a single bond which is linked to any one of $R^1$ to $R^4$ of an adjacent inorganic bridge through at least an oxygen atom.

When any one of $R^1$ to $R^4$ is a single bond which is linked to any one of $R^1$ to $R^4$ of an adjacent inorganic bridge through at least an oxygen atom, the linkage between the inorganic bridges (through at least an oxygen atom) is represented by the following formula (2):

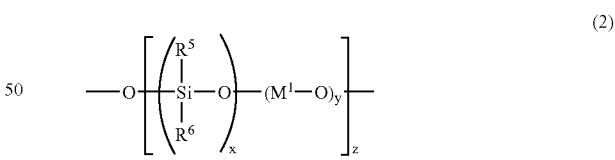

(2)

In the formula (2) above, each $M^1$ independently represents a divalent metal atom selected from the group consisting of beryllium, magnesium, calcium, strontium, barium, copper, zinc, nickel, iron, manganese, chromium and cobalt, and each of x, y and z is independently an integer of 0 or more. When x is 2 or more, $R^5$'s may be the same or different and $R^6$'s may be the same or different. When y is 2 or more, $M^1$'s may be the same or different. When z is 2 or more, x's may be the same or different, and y's may be the same or different.

With respect to $R^5$ and $R^6$, each of $R^5$ and $R^6$ may be independently any one of the atom and groups mentioned above as $R^1$, $R^2$, $R^3$ and $R^4$.

Specific examples of divalent groups represented by formula (2) above include the following atom and groups.
—O—,
—OSi(OH)$_2$OSiH$_2$O—,
—OSi(OH)$_2$O—,
—OSiH$_2$OSiH$_2$O—,
—OCaO—,
—OSi(OH)$_2$OSi(CH$_3$)$_2$O—,
—OMgO—,
—Si(CH$_3$)(OH)OSi(CH$_3$)$_2$O—,
—OCuO—,
—OSi(CH$_3$)$_2$OSi(CH$_3$)$_2$O—,
—OSiH(OH)O—,
—OSi(OH)$_2$OSiH$_2$O—,
—OSiH$_2$O—,
—OSiH(OH)OSiH$_2$O—,
—OSi(CH$_3$)(OH)O—,
—OSiH$_2$OSiH$_2$O—,
—OSi(CH$_3$)$_2$O—,
—OSi(OH)$_2$OSi(CH$_3$)$_2$O—,
—OSi(OH)$_2$OSi(OH)$_2$O—,
—Si(CH$_3$)(OH)OSi(CH$_3$)$_2$O—,
—OCaOSi(OH)$_2$O—,
—OSi(CH$_3$)$_2$OSi(CH$_3$)$_2$O—,
—OMgOSi(OH)$_2$O—,
—OSi(CH$_3$)(OH)OSi(OH)$_2$O—,
—OCuOSi(OH)$_2$O—,
—OSi(OH)$_2$OCaOSi(OH)$_2$O—,
—OSiH(OH)OSi(OH)$_2$O—,
—OSi(OH)$_2$OMgOSi(OH)$_2$O—,
—OSiH$_2$OSi(OH)$_2$O—,
—OSi(OH)$_2$OCuOSi(OH)$_2$O—,
—OSi(CH$_3$)(OH)OSi(OH)$_2$O—,
—OCaOSi(OH)$_2$OCaO—,
—OSi(CH$_3$)$_2$OSi(OH)$_2$O—,
—OMgOSi(OH)$_2$OMgO—,
—OSi(OH)$_2$OSiH(OH)O—,
—OCuOSi(OH)$_2$OCuO—,
—OSiH(OH)OSiH(OH)O—,
—OSiH$_2$OSiH(OH)O—,
—OSi(OH)$_2$OSi(CH$_3$)(OH)O—,
—Si(CH$_3$)(OH)OSi(CH$_3$)(OH)O—, and
—OSi(CH$_3$)$_2$OSi(CH$_3$)(OH)O—.

With respect to the above examples, the hydrogen atom of each of the hydroxyl group per se and the hydroxyl groups of the hydroxyl group-containing groups may independently be replaced by an alkali metal atom or a quaternary ammonium group. Further, with respect to the group having a plurality of hydroxyl groups, the hydrogen atom of each of the hydroxyl groups may independently be replaced by an alkali metal atom or a quaternary ammonium group.

As a representative example of the structure of the divalent group represented by formula (2) above, there can be mentioned a structure in which z=0, a structure in which x=0 and y=z=1.

Further, two of R$^1$, R$^2$, R$^3$ and R$^4$ in formula (1) above may be single bonds which are, respectively, linked to the terminal oxygen atoms of the divalent group of formula (2) above, to thereby form a ring. When at least one of r and t in formula (1) above is 2 or more, two R$^1$'s, two R$^2$'s, two R$^3$'s or two R$^4$'s in formula (1) above may be single bonds which are, respectively, linked to the terminal oxygen atoms of the divalent group of formula (2) above, to thereby form a ring.

The monovalent, siloxane linkage-containing group, which is used as any of R$^1$ to R$^4$, is a group which has a structure in which each of x and z in formula (2) above independently represents an integer of 1 or more, and a hydrogen atom or a silicon-containing group represented by SiR$^7_3$ (each R$^7$ independently represents a hydrogen atom or a monovalent organic group) is bonded to a free terminal of the group of formula (2), which terminal is not bonded to the silicon atom in formula (1), or a group which has a structure in which z=0 in formula (2) and a silicon-containing group represented by SiR$^7_3$ (each R$^7$ is as defined above) is bonded to a free terminal of the group of formula (2), which terminal is not bonded to the silicon atom in formula (1). (Examples of the above-mentioned monovalent organic group include the same groups as mentioned below as examples of the monovalent organic groups which can be used as any of R$^1$ to R$^4$.) When the hybrid material of the present invention is used as a material (such as a hydrophilicity reagent) which is desired to exhibit high hydrophilicity, it is preferred to use a monovalent, siloxane linkage-containing group which has a structure in which each of x and z in formula (2) above independently represents an integer of 1 or more and a hydrogen atom or a silicon-containing group represented by SiR$^7_3$ (each R$^7$ independently represents a hydrogen atom or a monovalent C$_1$–C$_5$ organic group) is bonded to a free terminal of the group of formula (2), which terminal is not bonded to the silicon atom in formula (1); and/or a monovalent, siloxane linkage-containing group which has a structure in which z=0 in formula (2) above and a hydrogen atom or a silicon containing group represented by SiR$^7_3$ (each R$^7$ independently represents a hydrogen atom or a monovalent C$_1$–C$_5$ organic group) is bonded to a free terminal of the group of formula (2), which terminal is not bonded to the silicon atom in formula (1). It is most preferred to use the former, in which a hydrogen atom is bonded to the above-mentioned free terminal of the group of formula (2). Specific examples of monovalent, siloxane linkage-containing groups include the following groups:
—OSi(OH)$_3$,
—OSi(CH$_3$)(OH)OSi(CH$_3$)(OH)$_2$,
—OSiH(OH)$_2$,
—OSi(CH$_3$)$_2$OSi(CH$_3$)(OH)$_2$,
—OSiH$_2$(OH),
—OSi(OH)$_2$OSiH$_2$(OH),
—OSi(CH$_3$)(OH)$_2$,
—OSiH(OH)OSiH$_2$(OH),
—OSi(CH$_3$)$_2$(OH),
—OSiH$_2$OSiH$_2$(OH),
—OSi(OH)$_2$OSi(OH)$_3$,
—OSi(OH)$_2$OSi(CH$_3$)$_2$(OH),
—OCaOSi(OH)$_3$,
—OSi(CH$_3$)(OH)OSi(CH$_3$)$_2$(OH),
—OMgOSi(OH)$_3$,
—OSi(CH$_3$)$_2$OSi(CH$_3$)$_2$(OH),
—OCuOSi(OH)$_3$,
—OSi(OH)$_2$OSiH$_3$,
—OSiH(OH)OSi(OH)$_3$,
—OSiH(OH)OSiH$_3$,
—OSiH$_2$OSi(OH)$_3$,
—OSiH$_2$OSiH$_3$,
—OSi(CH$_3$)(OH)OSi(OH)$_3$,
—OSi(OH)$_2$OSi(CH$_3$)$_3$,
—OSi(CH$_3$)$_2$OSi(OH)$_3$,
—OSi(CH$_3$)(OH)OSi(CH$_3$)$_3$,
—OSi(OH)$_2$OSiH(OH)$_2$,
—OSi(CH$_3$)$_2$OSi(CH$_3$)$_3$,
—OSiH(OH)OSiH(OH)$_2$,
—OSi(CH$_3$)(OH)OSi(OH)$_3$,
—OSiH$_2$OSiH(OH)$_2$,
—OSi(OH)$_2$OCaOSi(OH)$_3$, —OSi(OH)$_2$OSi(CH$_3$)(OH)$_2$,
—OSi(OH)$_2$OMgOSi(OH)$_3$, and
—OSi(OH)$_2$OCuOSi(OH)$_3$.

With respect to the introduction of the monovalent organic group used as any of R$^1$ to R$^4$ into the hybrid material of the present invention, the introduction is generally conducted by using an organosilicon compound, such as a silane coupling agent which comprises a silicon atom having bonded thereto an organic group (bonded to the silicon atom through a carbon atom thereof) and an alkoxy group. Specific examples of monovalent organic groups include non-reactive organic groups, such as aliphatic hydrocarbon groups (e.g., a methyl group, an ethyl group, a n-propyl group, an i-propyl group, a n-butyl group, an i-propyl group and a cyclohexyl group), aromatic hydrocarbon groups (e.g., a benzyl group), holagenated hydrocarbon groups (e.g., a 3-chloropropyl group); and reactive functional group-containing organic group, such as addition-polymerizable groups (each of which can be directly bonded to the silicon atom in formula (1)) (e.g., a vinyl group and a 3-(meth)acryloxypropyl group), addition-polymerizable groups having a structure in which a part of the above-mentioned non-reactive group is replaced by a vinyl group or a 3-(meth)acryloxypropyl group, epoxide-containing groups having a structure in which a part of the above-mentioned non-reactive group is replaced by a 3-glycidoxypropyl group or a 2-(3,4-epoxycyclehexyl) group; a primary or secondary amino group-containing group, which has a structure in which a part of the above-mentioned non-reactive group is replaced by a 3-aminopropyl group or a N-(2-aminoethyl)-3-aminopropyl group. With respect to each of these monovalent organic groups, the carbon atom at the terminal thereof is bonded to the silicon atom in formula (1). In the case of the above-mentioned non-reactive organic groups, such as aliphatic hydrocarbon groups, aromatic hydrocarbon groups and halogenated hydrocarbon groups, the use thereof is expected to have effects, such as the improvement in the solubility of the hybrid material in a resin; however, when the molecular weight of the organic group used is too high, the solubility of the organic group used in an aqueous medium (which is used in the production of the hybrid material of the present invention) is markedly lowered, thereby rendering difficult the production of the hybrid material. Therefore, it is preferred that the molecular weight of each of the non-reactive organic groups is 300 or less, more advantageously 100 or less. On the other hand, in the case of the above-mentioned reactive functional group-containing organic groups, the use thereof as any of R$^1$ to R$^4$ is expected to have effects such that, when the hybrid material is mixed with a resin, the organic groups react with functional groups of the resin, thereby strongly bonding the hybrid material to the resin. Further, in the case of the reactive functional group-containing organic group, the solubility thereof in an aqueous medium is generally high as compared to that of the above-mentioned non-reactive functional groups, and therefore, the molecular weight of the reactive functional group-containing organic group may be relatively high. Specifically, the molecular weight of the reactive functional group-containing organic group is preferably 500 or less, more preferably 300 or less, still more preferably 150 or less.

In the hybrid material of the present invention, the inorganic bridge may have various structures so long as the requirements of the present invention are satisfied. Specific examples of structures of the inorganic bridge include those shown in FIGS. 1 to 3.

In the present invention, with respect to each of the inorganic bridges of the inorganic domain, it is necessary that the oxygen atom of at least one siloxane linkage present in the inorganic bridge be chemically bonded to the divalent metal atom. The structure of such inorganic bridge in which the anionic siloxane group and the cationic divalent metal are bonded to each other is advantageous, for example, in that, as described above, the inorganic bridge can be chemically bonded to each of a polymer having a cationic functional group and a polymer having an anionic functional group. The inorganic bridges usable in the present invention can be categorized into the following three types: (a) an inorganic bridge in which both ends thereof are, respectively, bonded to anionic functional groups, (b) an inorganic bridge in which both ends thereof are, respectively, bonded to cationic functional groups, and (c) an inorganic bridge in which the ends thereof are, respectively, bonded to an anionic functional group and a cationic functional group. With respect to these three types of the inorganic bridge, most basic structures thereof are illustratively shown below (R$^1$ to R$^4$ are omitted, and each M represents a divalent metal atom):

(a) anionic functional group-M—O—Si—O—M-anionic functional group,
(b) cationic functional group-O—Si—O—M—O—Si—O-cationic functional group, and
(c) anionic functional group-M—O—Si—O-cationic functional group.

Figure 2:
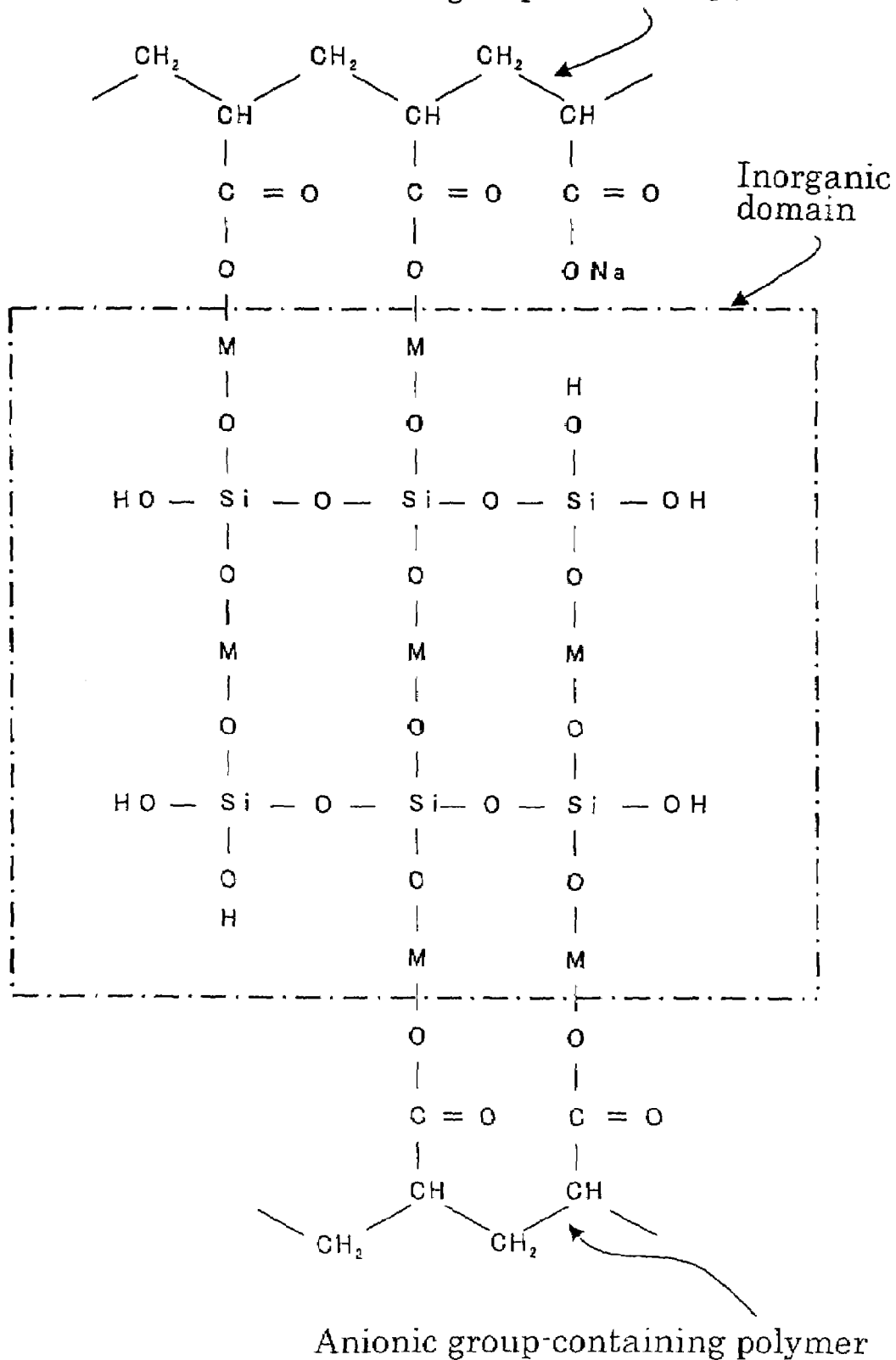
FIG. 2 is an explanatory diagram showing the structure of another embodiment of the organic domain/inorganic domain hybrid material of the present invention, in which each end of an inorganic bridge is bonded to an anionic functional group of an organic polymer.
Figure 3:
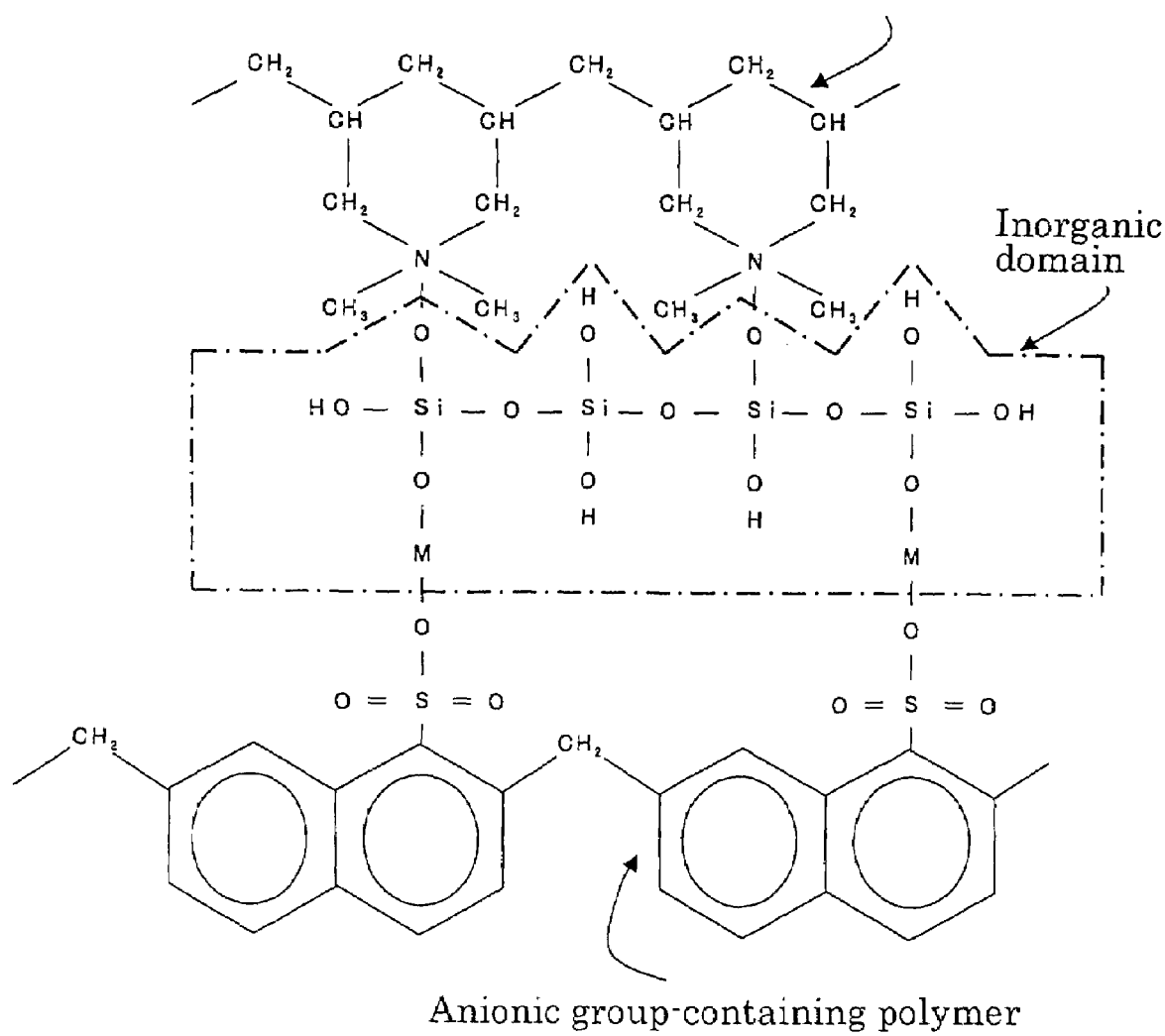
FIG. 3 is an explanatory diagram showing the structure of still another embodiment of the organic domain/inorganic domain hybrid material of the present invention, in which ends of an inorganic bridge are, respectively, bonded to an anionic functional group of an organic polymer and a cationic functional group of an organic polymer.

The structures shown in FIGS. 1 to 3 correspond to the above-mentioned types (a) to (c), respectively.

With respect to the atomic ratio of the divalent metal atoms (M) to the silicon atoms (Si) of the —O—Si—O— linkages, there is no particular limitation. However, the M/Si atomic ratio is preferably in the range of from 0.001 to 5.0, more preferably from 0.01 to 3.0, still more preferably from 0.1 to 1.5. Further, as mentioned above, the form of linkage between the organic domain and the inorganic domain varies depending on the ionic character of the organic polymer. In view of this, when an anionic organic polymer is used, it is most preferred that the M/Si atomic ratio is in the range of from 0.3 to 1.5, whereas, when a cationic organic polymer is used, it is most preferred that the M/Si atomic ratio is in the range of from 0.1 to 1.0. The M/Si atomic ratio can be determined, for example, by a method in which the values obtained by subjecting the hybrid material to fluorescence X-ray spectrometry are converted using a calibration curve separately prepared.

The divalent metal atom used in the inorganic domain of the hybrid material of the present invention is a metal atom which stably maintains the state of a divalent ion in an aqueous medium. In the present invention, the inorganic domain contains at least one divalent metal atom selected from the group consisting of beryllium, magnesium, calcium, strontium, barium, copper, zinc, nickel, iron, manganese, chromium and cobalt. These divalent metals may be used individually or in combination.

When at least a part of the divalent metal atoms in the inorganic domain of the hybrid material is magnesium, the solubility of the inorganic domain in an aqueous medium becomes low, so that it is likely that the inorganic domain of the hybrid material exhibits advantageously high stability during a long-term exposure of the hybrid material to air. On the other hand, when at least a part of the divalent metal atoms in the inorganic domain is strontium, the crystallinity of the inorganic domain can be easily controlled by appropriately choosing the production conditions of the hybrid material. When at least a part of the divalent metal atoms in the inorganic domain is at least one transition metal atom selected from the group consisting of copper, zinc, nickel, iron, manganese, chromium and cobalt, it becomes possible not only to impart the hybrid material with functional properties, such as antibacterial/antifungal property, but also to cause the hybrid material to have a color characteristic of the transition metal ion (e.g., blue, green or a color therebetween in the case of copper; green in the case of nickel; and bluish purple, reddish purple or a color therebetween in the case of cobalt). Further, by using these atoms in combination, it becomes possible to impart the hybrid material with a plurality of different functions and/or to control the color of the hybrid material. Therefore, it is preferred to use at least two types of metals in combination. In the case where at least two types of metals are used in combination, it is preferred to use calcium as one of the metals depending on the use of the hybrid material. The reason for this is as follows. When a part of the divalent metal atoms in the inorganic domain is calcium, the hybrid material exhibits high affinity for the calcium silicate present in cement and a cured form thereof, and hence, the hybrid material can be advantageously used for imparting various functions to a cured form of calcium silicate and the like.

Thus, the divalent metal atoms of the inorganic domain can be appropriately selected according to desired functions of the hybrid material of the present invention.

The divalent metal atoms can be introduced into the hybrid material by using compounds, such as a nitrate, a sulfate, an acetate, a chloride, a hydroxide, an oxide and a carbonate, as raw materials. With respect to such compounds used as raw materials, it is preferred to use those which have a solubility of 1% by weight or more in a solvent (aqueous medium) used in the below-described production of the hybrid material, since the divalent metals can be easily introduced into the hybrid material in the form of ions. It is more preferred that the solubility of the compounds is 5% by weight or more. The compounds used as raw materials of the divalent metal atoms can also be appropriately selected according to the use of the hybrid material. For example, when the hybrid material of the present invention is used as a hydrophilicity reagent, it is sometimes most preferred to use a nitrate as a raw material.

With respect to a source of the silicon atom, there is no particular limitation so long as the source can form a silicate anion in an aqueous medium. Examples of sources of the silicon atom include silicate compounds and silicon halides. Representative examples of silicate compounds include inorganic silicate compounds, such as silicates (e.g., sodium o-silicate and sodium m-silicate), silicic acid, and silica; and organic silicon compounds, such as alkoxides (e.g., tetraethoxysilane, tetramethoxysilane and various silane coupling agents). Representative examples of silicon halides include silicon tetrachloride. Of these compounds, preferred are silicates of alkali metals (such as sodium o-silicate and sodium m-silicate), silicic acid, a colloidal silica, and silicon halides, because these compounds can be handled with ease and obtained at a low cost. Further, the above-mentioned silicates of alkali metals include water glass Nos. 1, 2 and 3 which are commercially employed and are specified in the Japan Industrial Standard (JIS K 1408-66).

In the inorganic bridges of the hybrid material of the present invention, at least a portion of the silicon atoms are bonded to the divalent metal atom through an oxygen atom. In the analysis of the hybrid material by infrared spectroscopy, a peak in the absorbance ascribed to the —Si—O—M— linkage (formed by the silicon (Si) atom, the oxygen (O) atom and the divalent metal (M) atom) is observed at a wave number which is smaller than the wave number at which a peak in the absorbance ascribed to the —Si—O—Si— linkage is observed. With respect to such a shift of the peak in the absorbance, an explanation is made below. In the infrared spectroscopy of a structure (e.g., silica gel) which contains a plurality of siloxane linkages (i.e., —O—Si linkages), wherein almost all of the siloxane linkages are bonded to further silicon atoms to form —Si—O—Si— linkages, a peak in the absorbance ascribed to the siloxane linkages is observed around 1,090 $cm^{-1}$. On the other hand, when, as in the case of the hybrid material of the present invention, such a structure further contains a —Si—O—M— linkage, a peak in the absorbance ascribed to the siloxane linkages shifts to a lower wave number. For example, when a structure contains strontium atoms or calcium atoms as the divalent metal atom M's, a peak in the absorbance ascribed to the —O—Si—O— linkage (i.e., a pair of siloxane linkages) shifts to 970 $cm^{-1}$. Needless to say, the degree of the shift of the peak in the absorbance ascribed to the —O—Si—O— linkage in the infrared spectroscopy depends on the type and amount of the divalent metal (M) atom forming the —Si—O—M— linkage. However, so long as the divalent metal (M) atom forms the —Si—O—M— linkage, the peak in the absorbance ascribed to the —O—Si—O— linkage shifts to a wave number smaller than about 1,090 $cm^{-1}$, irrespective of the type and amount of the divalent metal (M) atom. In the present invention, by virtue of the presence of the —Si—O—M— linkage, it is possible to form and break the linkage between the divalent metal atom and the oxygen atom of the —O—Si—O— linkage in a reversible manner depending on the pH.

Further, the hybrid material of the present invention has a characteristic feature that most of the silicon atoms in the hybrid material do not form a three-dimensional structure but form a linear structure. Such a linear structure can be confirmed by analyzing the hybrid material by $^{29}$Si nuclear magnetic resonance spectroscopy (NMR method) to obtain the intensity ratio of the peaks which are, respectively, ascribed to the different siloxane structures to which another silicon atom(s) is or are bonded. More specifically, the ratio of the silicon-containing linear structure can be calculated from the intensities of the following three peaks: a peak (Q1) observed around a chemical shift of 75 ppm, which is ascribed to a siloxane linkage to which one silicon atom is bonded, a peak (Q2) observed around a chemical shift of 85 ppm, which is ascribed to a siloxane linkage to which two silicon atoms are bonded, and a peak (Q3+Q4) observed around a chemical shift of 95 ppm, which is ascribed to a siloxane linkage to which three or more silicon atoms are bonded. In the present invention, it is characteristic of the hybrid material that the peak intensity ratio: (Q1+Q2)/(Q3+Q4) is 0.3 or more, and this ratio is generally 0.5 or more. That is, it is characteristic of the inorganic domain of the hybrid material of the present invention that, when the hybrid material is analyzed by $^{29}$Si nuclear magnetic resonance spectroscopy (NMR method), the peak intensity ratio: (Q1+Q2)/(Q3+Q4) is 0.3 or more, and it is preferred that the peak intensity ratio is 0.5 or more. When the above-mentioned peaks overlap, the peak intensity ratio is determined by the conventional waveform separation method. Thus, by virtue of the linear siloxane structure, the inorganic domain has a large number of sites to which the organic polymer can be bonded, thereby facilitating the formation of the hybrid material. Specifically, an anionic organic polymer is bonded to the inorganic domain through a divalent metal atom which is linked to the siloxane linkage of the inorganic bridge, whereas a cationic polymer is directly bonded to the siloxane anion of the inorganic bridge. On the other hand, when many silicon atoms share many oxygen atoms to form a planer structure, the number of sites for the reaction between the siloxane linkage and the organic polymer is decreased. Therefore, for preventing decrease in the number of such reaction sites, it is preferred that the siloxane linkages form a linear structure. Further, for example, when the hybrid material of the present invention is used as a material (such as a hydrophilicity reagent) which is desired to exhibit high hydrophilicity, the presence of many terminal siloxane groups in the inorganic domain further improves the hydrophilicity of the hybrid material of the present invention.

In the present invention, it is also a characteristic of the hybrid material that, as mentioned above, a plurality of different divalent metal atoms can be used in combination in the inorganic domain. By using a plurality of different divalent metal atoms in combination, it is possible to obtain a multi-functional hybrid material simultaneously exhibiting characteristics ascribed to different metals. Further, by using a plurality of different divalent metal atoms in combination, crystallization behaviors of the different metals can be controlled to thereby achieve improved functions.

In the present invention, when at least a part of the divalent metal atoms of the inorganic domain is magnesium, the hybrid material has a characteristic that the inorganic domain is amorphous. In the present invention, "amorphous" means that, when the hybrid material is analyzed by wide-angle X-ray diffractiometry using CuKα ray, there is observed no crystalline peak having a half width of 6° or less between $2\theta=15°$ and $2\theta=55°$. In the above-mentioned hybrid material characterized in that at least a part of the divalent metal atoms of the inorganic domain is magnesium and that the inorganic domain is amorphous, there is occasionally observed a very broad peak around $2\theta=25°$ and around $2\theta=35°$. When the half width cannot be determined due to such a broad peak, for example, the half width can be determined by using a curve fitted by the piezone function.

When at least a part of the divalent metal atoms is magnesium, the component elements of the inorganic domain are similar to those of a natural clay or a synthesized clay. However, the above-mentioned "amorphous" feature and structure of the siloxane linkages clearly indicate that the inorganic domain has a structure different from that of a clay.

Further, when a part of the divalent metal atoms of the inorganic domain is magnesium and another divalent metal atom(s) (e.g., a calcium atom) is also present in the inorganic domain, there is sometimes observed a crystalline peak indicating the presence of a divalent metal atom other than a magnesium atom in the inorganic domain. When such a crystalline peak is observed, the divalent metal atom other than a magnesium atom is identified by the X-ray fluorescence spectrometry and the like, and the obtained crystalline peak pattern is compared with a reference crystalline peak pattern observed when the above-identified divalent metal atom is present in the inorganic domain, to thereby determine whether or not the observed crystalline peak indicates the presence of a divalent metal atom other than a magnesium atom. When it is determined that the crystalline peak indicates the presence of a divalent metal atom other than a magnesium atom, this also indicates that a part of the inorganic domain having magnesium atoms as the divalent metal atoms is amorphous.

Further, the inorganic domain of the hybrid material of the present invention may have a layered structure. With respect to the layered structure of the inorganic domain of the hybrid material, an explanation is made below. It is known that compounds, such as calcium silicate hydrate and calcium aluminate silicate hydrate, form a layered structure in which calcium (Ca) atoms and oxygen (O) atoms are arranged in at least one plane to form at least one CaO layer. The inorganic domain of the hybrid material of the present invention also can have a single-layer or multi-layer structure (in which the divalent metal atoms and the oxygen atoms are arranged in one or more planes) corresponding to that of calcium silicate hydrate. Further, as described below, the silicon atom of the inorganic domain may be replaced by an aluminum atom. Therefore, the inorganic domain can also have a single-layer or multi-layer structure corresponding to that of calcium aluminate silicate hydrate. The presence of the above-mentioned layered structure can be confirmed by using an X-ray diffractometer.

In the present invention, the formation of the chemical bond between the organic polymer domain and the inorganic domain can be confirmed by a method comprising washing well the hybrid material, followed by drying, and analyzing the resultant by infra-red spectroscopy. In the infra-red spectroscopy conducted with respect to the hybrid material of the present invention, an absorbance ascribed to the organic polymer (such as a hydrocarbon polymer) and an absorbance ascribed to the inorganic domain (such as a siloxane linkage) are observed, which means that the organic polymer domain and the inorganic domain are chemically bonded to each other.

The hybrid material of the present invention can contain at least one element other than elements of essential components of the hybrid material of the present invention. Examples of such other elements include alkali metals, such as sodium and potassium, and trivalent metals, such as aluminum and iron. Of these, aluminum is especially preferred, because an aluminum atom replaces a silicon atom in the inorganic material used for producing the hybrid material, and sometimes strengthens the bond between the inorganic material and a water-soluble organic polymer. With respect to the amount of aluminum atoms which replace the silicon atoms, it is preferred that 1 to 15% of silicon atoms are replaced by aluminum atoms. The replacement of the silicon atoms by the aluminum atoms can be confirmed, based on the signal shift observed in the analysis by $^{29}$Si nuclear magnetic resonance method (NMR method). Further, examples of sources of aluminum atoms include inorganic aluminum compounds, such as aluminum chloride and sodium aluminate, and aluminum alkoxides, such as triethoxyaluminum.

The hybrid material of the present invention can be put into practical use without washing the hybrid material. However, when it is intended to use the hybrid material in such a form that the solvent used in the production thereof and/or the unreacted raw materials have been removed, the hybrid material may be subjected to the following washing and drying operations (which can be also used for washing and drying the hybrid material subjected to the above-mentioned analyses).

The washing operation can be conducted as follows. The hybrid material can be washed with the same solvent as used in the production of the hybrid material. The solvent for washing is used in an amount which is at least about 100 times by weight the total weight of the raw materials (in terms of solids) used for producing the hybrid material, and a sequence of the washing operation and subsequent drying operation (described below) is repeated until the difference in dry weight between the hybrid material before washing and the hybrid material after washing becomes 10% or less.

The drying operation can be conducted as follows. The washed hybrid material is subjected to drying at 60° C. under a reduced pressure of 1 kPa or less until the weight of the hybrid material becomes constant (i.e., the change in weight of the hybrid material becomes 0.5% or less per hour).

When at least a part of the organic domain comprises at least one organic polymer having an anionic functional group and optionally a cationic functional group, the weight ratio of the organic domain to the inorganic domain is less than 1.0%. As mentioned above in connection with the molecular weight of the organic polymer, when the weight ratio is 1.0 or more, the produced hybrid material exhibits substantially no fluidity, thereby causing problems such that it becomes difficult to disperse the hybrid material uniformly in a polymer emulsion or the like.

With respect to the weight ratio of the organic domain to the inorganic domain, there is no particular lower limit so long as the presence of the organic domain can be confirmed by the above-mentioned infra-red spectroscopy. However, for obtaining remarkable effects of the combination of the organic domain and the inorganic domain, it is preferred that the ratio is 0.05 or more, more preferably 0.1 or more.

The organic domain/inorganic domain weight ratio can be measured by the following method with respect to the hybrid material which has been subjected to the above-mentioned washing operation and the above-mentioned drying operation, wherein the drying operation is conducted at 60° C. under a reduced pressure of 1 kPa or less until the weight of the hybrid material becomes constant as defined above.

First, the determination of each of the metal atoms and the silicon atoms can be conducted by X-ray fluorometry using a calibration curve prepared in advance. In the determination by X-ray fluorometry, the weights of the divalent metal atoms and the silicon atoms (which are components of the inorganic domain) are determined in terms of the weights of oxides thereof on the assumption that the divalent metal atoms and the silicon atoms are present in the form of oxides thereof. The total weight of the divalent metal atoms and the silicon atoms is defined as the weight of the inorganic domain. Separately, the hybrid material is heated in air by using an electric furnace to elevate the temperature of the hybrid material from room temperature to 1,000° C. at a rate of 25° C./min, followed by maintaining the temperature at 1,000° C. for 10 minutes, to thereby calcine the hybrid material. The resultant ash is analyzed by various elemental analyses. From the change in weight of the hybrid material, which is caused by the calcination, and the elemental ratio obtained by the elemental analyses, the weight of organic components ascribed to the organic polymer is obtained. The total weight of the organic components is defined as the weight of the organic domain. When carbon atoms are detected in the ash obtained by the calcination, the weight of the carbon atoms (in terms of methyl groups) is added to the weight of the organic domain. Further, when the alkali metal atoms, such as a lithium atom and a sodium atom, are detected in the ash, the weights of the alkali metal atoms are also added to the weight of the organic domain, because the organic polymer binds to such alkali metal atoms.

Further, when the hybrid material of the present invention contains aluminum atoms, the replacement of the silicon atoms by the aluminum atoms can be confirmed by the above-mentioned NMR method. Further, the determination of the aluminum atom can be conducted by the above-mentioned X-ray fluorometry as in the case of the determination of the silicon atom, and the determined weight of the aluminum atom (in terms of an oxide thereof) is added to the weights of the divalent metal atoms and the silicon atoms to obtain the weight of inorganic domain.

Hereinbelow, an explanation is made with respect to the process for producing the hybrid material of the present invention.

The hybrid material of the present invention can be produced by a process comprising contacting, in the presence of an aqueous medium and at a pH of 7 or more, the following chemical species (a), (b) and (c) with one another:

(a) silicate anions formed from a silicate compound or a silicon halide, (b) polymer ions formed from at least one water-soluble organic polymer having a plurality of functional groups, wherein each functional group is independently selected from the group consisting of an anionic functional group and a cationic functional group, and (c) divalent metal cations formed from a salt of at least one divalent metal selected from the group consisting of beryllium, magnesium, calcium, strontium, barium, copper, zinc, nickel, iron, manganese, chromium and cobalt, with the proviso that, when at least a part of the organic domain is comprised of at least one organic polymer having an anionic functional group and optionally a cationic functional group, or when the organic domain is comprised of at least one organic polymer having a cationic functional group and having no anionic functional group and when the weight ratio of the organic domain to the inorganic domain is less than 1.0, not all the divalent metal cations are simultaneously calcium cations.

When the hybrid material is used as a hydrophilicity reagent or an antibacterial/antifungal reagent, all the divalent metal cations as the chemical species (c) can be simultaneously calcium cations.

When the hybrid material is used as a hydrophilicity reagent or an antibacterial/antifungal reagent, at least a part of the organic polymer used to form the chemical species (b) (polymer ions) is comprised of at least one organic polymer having an anionic functional group and optionally a cationic functional group.

Further, as mentioned above, when an aluminum atom (optional element) is introduced into the hybrid material, an aluminate anion formed from an aluminum compound is contacted, as an additional chemical species (d), with the above-mentioned chemical species (a), (b) and (c).

With respect to the specific method for contacting each of the chemical species, there is no particular limitation so long as the formation of the ionic bond between the siloxane (—O—Si—O—) linkage and the divalent metal atom occurs in the presence of the water-soluble organic polymer or the formation of the ionic bond between the divalent metal atom and the functional group of the water-soluble organic polymer occurs in the presence of a silicon atom forming the —O—Si—O— linkage.

Specific examples of the method for contacting the above-mentioned chemical species include (1) a method comprising preparing a solution of a mixture of the water-soluble organic polymer and a silicate compound or a silicon halide, and adding a divalent metal compound to the solution, with the proviso that, when the solution has a pH of less than 7, the pH of the solution is adjusted to 7 or more by addition of a basic substance before the addition of the divalent metal compound, (2) a method comprising preparing, at a pH of less than 7, a solution of a mixture of a water-soluble organic polymer, a silicate compound or a silicon halide, and a divalent metal compound, and adding a basic substance to the solution to adjust the pH of the solution to 7 or more, (3) a method comprising preparing, in advance, a compound of a divalent metal compound with a silicate compound or a silicon halide, mixing the prepared compound with a water-soluble organic polymer under an acidic condition, and mixing the resultant mixture with an alkaline solution, (4) a method comprising preparing a solution of a mixture of a silicate compound or a silicon halide and a divalent metal compound under an acidic condition, followed by addition of an alkaline solution of a water-soluble organic polymer to obtain a mixture having a pH of 7 or more, and (5) a method comprising preparing an acidic liquid mixture of a water-soluble organic polymer and a divalent metal compound, followed by addition of an alkaline solution of a silicate compound or a silicon halide to obtain a mixture having a pH of 7 or more.

It is preferred that the contacting of the above-mentioned chemical species is conducted at a pH of 9 or more. With respect to the pH at which the chemical species are contacted, there is no particular upper limit. When, as the silicate compound, an organosilicon compound (e.g., an silicon alkoxide) is used, such an organosilicon compound is generally subjected to hydrolysis before use. The hydrolysis of the organosilicon compound can be conducted by any conventional methods. Needless to say, the hydrolysis proceeds in the presence of water. The hydrolysis of the organosilicon compound is generally promoted in an acidic atmosphere.

It is characteristic of the reaction for forming the hybrid material of the present invention that the reaction generally rapidly proceeds by mixing the chemical species at room temperature. When the organosilicon compound is used as a source of the silicon atoms forming the —O—Si—O— linkages, it is preferred that the organosilicon compound is subjected to hydrolysis prior to use, or the organosilicon compound is used under an acidic condition to thereby hydrolyze the organosilicon compound.

As examples of sources of the above-mentioned chemical species (a), (c) and (d), there can be mentioned the above-mentioned sources of the silicon atoms forming the —O—Si—O— linkages, the above-mentioned sources of the water-soluble organic polymer, the above-mentioned sources of the divalent metal atoms and the above-mentioned sources of aluminum, respectively.

The solvent (i.e., the above-mentioned aqueous medium) used in the above-mentioned process needs to contain water. It is preferred to use an aqueous medium containing water in an amount of 10% by weight or more at room temperature. As the aqueous medium, of course, water can be used. Alternatively, the aqueous medium may be a mixture of water with an organic solvent miscible with water, such as an alcohol (e.g., methanol or ethanol); a ketone (e.g., acetone or methyethylketone); an ester (e.g., ethyl acetate or butyl acetate); dimethyl formamide; dimethyl sulfoxide; and a mixture thereof. Also, various inorganic or organic salt or various surfactants may be mixed with the aqueous medium. In the production of the hybrid material, it is not required that the organic polymer be completely dissolved in the aqueous medium. However, for uniformly reacting the chemical species, it is preferred that the aqueous medium has a water content of 50% by weight or more and the organic polymer is completely dissolved in the aqueous medium. Examples of basic substances include alkali metal hydroxides, such as sodium hydroxide and potassium hydroxide, or aqueous solutions thereof, aqueous ammonia and amines. Examples of acidic substances used for rendering a reaction system acidic include mineral acids, such as hydrochloric acid and nitric acid, and organic acids, such as acetic acid and p-toluenesulfonic acid.

Alternatively, the hybrid material of the present invention can be also obtained by synthesizing the water-soluble organic polymer after or simultaneously with contacting the ions of the monomers which are raw materials of the above-mentioned water-soluble organic polymer having the hydrophilic functional group with silicate anions formed from a silicate compound or a silicon halide, divalent metal cations formed from a divalent metal salt, and optionally aluminate anions formed from an aluminum compound.

Hereinbelow, explanations are made with respect to the specific uses of the hybrid material of the present invention.

The hybrid material of the present invention may be used alone as a functional material or may be used as an additive in combination with an organic or inorganic matrix. In the present invention, the term "matrix" is used as a generic name for substances to which the hybrid material of the present invention is added.

With respect to the hybrid material of the present invention, which is obtained by the above-mentioned production process, the hybrid material may be put into practical use after removing the solvent used in the production process and/or the unreacted raw materials by the above-mentioned washing and drying operations. Needless to say, the produced hybrid material which contains the solvent and/or the unreacted raw materials may be put into practical use without conducting the above-mentioned washing and drying operations. Alternatively, prior to use of the produced hybrid material, the solvent used in the production process and/or the unreacted raw materials are removed from the hybrid material, followed by impregnation of the hybrid material with a solvent, such as water.

The hybrid material can be used as an additive for an organic matrix and an inorganic matrix. Examples of organic matrices include aqueous or oil coating compositions, and film-forming components (such as a polymer emulsion) of the coating compositions; waxes; films of organic polymers; and resins. Examples of inorganic matrices include cements and cured forms thereof; ceramics; and glasses. Thus, it is also a characteristic of the organic domain/inorganic domain hybrid material of the present invention that the hybrid material can be advantageously used in the form of a mixture thereof with an organic or inorganic matrix. Further, the hybrid material can also be used to form a coating on an organic or inorganic substrate made of a metal, a ceramic, a glass, a cured form of a cement, a resin or the like. The coating may be formed by, for example, application of the hybrid material to the substrate. In this case, the hybrid material may be used alone or in the form of a mixture thereof with any of the above-mentioned matrices.

Of the above-mentioned matrices, preferred are organic matrices, such as aqueous coating compositions, and aqueous organic polymer dispersions used as raw materials for the aqueous coating compositions. These matrices are preferred for the following reason. The hybrid material of the present invention comprises water-soluble or hydrophilic materials, and hence, the hybrid material can be easily and uniformly dispersed in aqueous coating compositions and raw materials thereof (i.e., aqueous organic polymer dispersions), each of which uses water as a solvent or a dispersion medium. As an especially preferred matrix, there can be mentioned a polymer emulsion (an aqueous organic polymer dispersion) which is widely sold as "emulsion" or "latex". With respect to such a polymer emulsion, generally, polymer particles are stably dispersed in an aqueous medium, and hence, the emulsion is capable of forming a film by fusion-bonding of the polymer particles which is caused by the removal of the aqueous medium from the emulsion. The diameter of organic polymer particles dispersed in the aqueous medium is generally in the range of from 1 to 2,000 nm, preferably 10 to 1,000 nm, more preferably from 10 to 500 nm.

With respect to a method for producing the polymer emulsion, there is no particular limitation. For example, the polymer emulsion can be produced by a method comprising copolymerizing an anionic functional group-containing monomer or a cationic functional group-containing monomer with a comonomer by emulsion polymerization. Examples of anionic functional group-containing monomers include (meth)acrylic acid and salts thereof, itaconic acid and salts thereof, fumaric acid and salts thereof, maleic acid and salts thereof, crotonic acid and salts thereof, maleic anhydride, itaconic acid and salts thereof, maleic acid and half ester of salts thereof, styrenesulfonic acid and salts thereof and allylsulfosuccinic acid and salts thereof. Examples of nonionic functional group-containing monomers include hydroxyethyl (meth)acrylate, hydroxypropyl (meth)acrylate, hydroxybutyl (meth)acrylate, hydroxycyclohexyl (meth)acrylate, 4-hydroxy butyl vinyl ether, and a half ester of any of these hydroxyl group-containing monomers with a cyclic acid anhydride, such as succinic acid anhydride. Examples of comonomers include (meth)acrylic esters, such as methyl (meth)acrylate, ethyl (meth)acrylate, butyl (meth)acrylate, 2-ethylhexyl (meth)acrylate, dodecyl (meth)acrylate, cyclohexyl (meth)acrylate; aromatic monomers, such as styrene, a-methylstyrene and vinyltoluene; vinyl esters, such as vinyl acetate, vinyl propionate and vinyl versatate; vinyl ethers, such as ethyl vinyl ether, butyl vinyl ether or cyclohexyl vinyl ether; vinyl cyanides, such as (meth)acrylonitrile; vinyl halides, such as vinyl chloride, vinylidene chloride, vinylidene fluoride, tetrafluoroethylene, chlorotrifluoroethylene and hexafluoropropylene; and butadiene.

With respect to a hydrophilic coating composition prepared by mixing any of the above-mentioned polymer emulsions with the hybrid material of the present invention, the coating composition has all of the functional properties of the hybrid material, such as hydrophilicity and antibacterial/antifungal property. As a representative functional property of the hydrophilic coating composition, there can be mentioned high hydrophilicity of a coating formed from the hydrophilic coating composition. In other words, the hybrid material of the present invention functions as an excellent hydrophilicity reagent. Such a hydrophilic coating composition of the present invention is advantageous in that the coating composition does not require cumbersome operations, such as a double coating operation and a mixing of the liquid components of the coating composition at the time of the use of the coating composition, thus exhibiting excellent workability.

With respect to the hydrophilic coating formed from the above-mentioned hydrophilic coating composition, by virtue of the hydrophilicity thereof, the coating exhibits stain resistance such that it is possible, for example, to prevent the coating from getting tarnished by the adhesion of very small waterdrops, to prevent a scattering of the light caused by waterdrops on the coating, and to make it easy to wash away dirt attached to the coating. Especially, the hydrophilic coating is effective for preventing occurrence of the so-called "raindrop dirt" (i.e., oily dirt adhering to the coating, which is formed along the path of flow of a raindrop). As a preferred example of polymer emulsions (aqueous organic polymer dispersions) used to produce a hydrophilic coating composition which is used for coating an outer wall of a building and is capable of preventing occurrence of the raindrop dirt, there can be mentioned a (meth) acrylate polymer emulsion (the so-called acrylic emulsion). It is also preferred to use an acrylstyrene emulsion or the so-called acrylsilicone type emulsion which is a silicon-modified emulsion. The polymer emulsion can be appropriately selected depending on the desired wheatherability and the cost.

With respect to the hydrophilic coating composition of the present invention, by addition of the hydrophilicity reagent to the polymer emulsion, it is possible to form a coating having an improved hydrophilicity. In the present invention, the improvement of hydrophilicity is evaluated as follows. With respect to each of a coating obtained from the polymer emulsion alone and a coating obtained from the hydrophilic coating composition, the contact angle of a waterdrop against the coating is measured. When the contact angle measured with respect to the coating formed from the hydrophilic coating composition is smaller than the contact angle measured with respect to the coating formed from the polymer emulsion alone by 5° or more, it is judged that the hydrophlicity of the coating is improved by the addition of the hybrid material of the present invention. It is preferred that the contact angle measured with respect to the coating formed from the hydrophilic coating composition is smaller than the contact angle measured with respect to the coating formed from the polymer emulsion alone by 10° or more. The above-mentioned contact angle of a waterdrop varies depending on the conditions (such as drying temperature and drying time) for forming the coating. Therefore, when the drying is conducted at room temperature, the above-mentioned evaluation of the improvement of the hydrophilicity of the coating is conducted using the contact angle values obtained with respect to the above-mentioned two coatings after each of the coatings is dried, such that a further drying of the coating would not cause a change in the contact angle. Alternatively, in order to conduct a fair comparison between the above-mentioned two coatings, the evaluation may be conducted using the contact angle values measured with respect to the above-mentioned two coatings which are dried by heating under the same conditions wherein the drying temperature is 90° C. or less. In the case where the drying of the coatings is conducted by heating, the appropriate timing for obtaining the contact angle values used for the evaluation of the hydrophilicity varies depending on the heating temperature and the heating time. However, generally, the evaluation of the hydrophilicity is conducted using the contact angle values obtained after allowing the heated coatings to stand for a sufficient period of time (e.g., 12 hours) to render constant the contact angle values of the coatings. Further, when the hydrophilic coating composition is used as a coating composition (such as a stain resistant coating composition) which is designed to exhibit desired functions when a coating formed from the coating composition is exposed to the rainwater, the improved hydrophilicity of the coating can be confirmed by visually observing that the coating does not repel the rainwater.

In the hydrophilic coating composition of the present invention, there is no particular limitation with respect to the ratio of the polymer emulsion to the hydrophilicity reagent. However, when the amount of the hydrophilicity reagent is too large, the water resistance of a coating formed from the coating composition is sometimes lowered, and hence, the polymer emulsion/hydrophilicity reagent weight ratio (in terms of the dried solids) is preferably 0.5 or more, more preferably 1 or more, still more preferably 2 or more, most preferably 5 or more. There is no particular upper limit with respect to the above-mentioned weight ratio so long as the coating formed from the coating composition exhibits the above-mentioned improved hydrophilicity.

Further, with respect to the coating comprising the hydrophilicity agent (the hybrid material of the present invention) and the polymer emulsion, when the polymer emulsion is used as an auxiliary reagent for forming a coating, the amount of the polymer emulsion may be lower than mentioned above. Specifically, in such a case, the polymer emulsion/hydrophilicity reagent weight ratio may be 0.01 or more, more preferably 0.1 or more.

The hydrophilic coating composition of the present invention can be used in the form of a mixture thereof with a substance (such as a surfactant or a low molecular weight compound) other than the polymer emulsion and the hydrophilicity reagent, for the purpose of controlling the film forming temperature, improving the dispersion stability and adjusting the pH.

If desired, the hydrophilic coating composition of the present invention may further contain a conventional pigment or pigment dispersion. Such a coating composition can be used to form a colored, hydrophilic coating.

With respect to the hydrophilic coating formed from the hydrophilic coating composition of the present invention, the contact angle of a water drop against the coating is generally 70° or less, more preferably 65° or less, still more preferably 60° or less, most preferably 55° or less. As mentioned above, when the hydrophilic coating is used as a coating which is designed to exhibit desired functions when the coating is exposed to the rainwater, the improved hydrophilicity of the coating can be confirmed by visually observing that the coating does not repel the rainwater.

The above-mentioned hydrophilic coating is formed by a method comprising applying the hydrophilic coating composition to a substrate, followed by drying. With respect to the specific method for the application and subsequent drying, there is no particular limitation and the method is appropriately selected according to the conditions under which the formation of the coating is conducted. The above-mentioned hydrophilic coating (obtained by applying the hydrophilic coating composition of the present invention to a substrate, followed by drying) can be used not only in the field of coatings, such as a stain resistant coating, an antifouling coating, a fog resistant coating and a coating capable of preventing the formation of waterdrops, but also can be used as a material for a non-image portion of a lithography plate.

Further, when the hybrid material of the present invention is used in the form of a mixture thereof with a polymer emulsion (aqueous dispersion of the organic polymer), the hybrid material also functions as a matting reagent which can impart to another material hydrophilicity and stain resistance. This function is influenced by the type of the polymer emulsion; however, this function becomes remarkable when the hybrid material used has an organic domain comprising a polymer having a cationic functional group, such as a quaternary ammonium salt.

The hybrid material of the present invention has many functions, and, generally, has especially excellent ability to impart to another material hydrophilicity. Specifically, the hybrid material of the present invention can be used to form a coating having a surface which exhibits strong hydrophilicity, i.e., the contact angle of a waterdrop against such a surface is 20° or less. Therefore, when the hybrid material is added to the above-mentioned organic or inorganic matrix, the hybrid material improves the hydrophilicity of the matrix in addition to other properties of the matrix. As mentioned above in connection with the coating composition comprising a polymer emulsion as the matrix, when the waterdrop contact angle measured with respect to the coating formed from the composition comprising the hybrid material and the matrix is smaller than the waterdrop contact angle measured with respect to the coating formed from the matrix alone by 5° or more, it is judged that the hydrophilicity of the matrix is improved by the addition of the hybrid material of the present invention. In such a case, it can be judged that the hybrid material of the present invention functions as a hydrophilicity reagent irrespective of whether or not the property intended to be imparted to the matrix is hydrophilicity.

When the main object of the use of the hybrid material of the present invention is to impart hydrophilicity to a matrix, such object can be attained also when the hybrid material is used with a matrix other than the above-mentioned polymer emulsion. For example, a coating composition comprising the hybrid material of the present invention is applied to a glass surface or a resin surface for the purpose of preventing the occurrence of fog on the surface; or it can be applied to a door mirror of a car for the purpose of preventing a diffused reflection of the light caused by water drops, for example, inorganic binders obtained using a sol-gel reaction can be advantageously used as a matrix of the composition. Also, for example, when a coating composition comprising the hybrid material of the present invention is used for preventing waterdrops from attaching to a face shield of a motorcycle helmet (which waterdrops cause a diffused reflection of the light), a transparent resin (used for producing the face shield of a motorcycle helmet) can also be advantageously used as a matrix of the composition. Further, utilizing the stain resistance of the hybrid material of the present invention, the hybrid material can be used in combination with a wax for automobiles to prevent a car from getting dirty. When the hybrid material of the present invention is used in the form of a coating composition comprising the hybrid material and the above-mentioned matrix, which is applied to a surface of a substrate, the matrix can be appropriately selected taking into consideration the removability of the resultant coating after use thereof. Further, the hybrid material can be used alone depending on the intended use thereof.

Further, with respect to the inorganic matrix used in the case where the hybrid material of the present invention is used as an additive, it is preferred to use cements and cured forms thereof for the following reason. The cements undergo curing reaction in the presence of an aqueous medium, so that cements are generally used in the form of a mixture thereof with an aqueous medium. As mentioned above, the hybrid material of the present invention is comprised of a water-soluble or hydrophilic material. Therefore, cements and cured forms thereof, which are used with an aqueous medium, can be advantageously used as matrices to which the hybrid material of the present invention is added.

When the hybrid material of the present invention is mixed with cements and/or cured forms thereof as an additive, of course, the functional properties of the hybrid material of the present invention are imparted to the cements and/or cured forms thereof. As a representative example of such functional properties, there can be mentioned antibacterial/antifungal property.

The hybrid material of the present invention exhibits antibacterial/antifungal property depending on the composition thereof. In the present invention, the term "antibacterial/antifungal property" means an ability to exhibit a killing effect or a propagation suppressing effect with respect to at least one microbe selected from the group consisting of bacteria and fungi. The antibacterial/antifungal property can be obtained when at least one organic polymer having a cationic functional group and optionally an anionic functional group is used as at least a part of the organic domain, or when at least one organic polymer (exemplified below) having a monomer unit having an antibacterial/antifungal functional group and an anionic functional group is used as at least a part of the organic domain. Also, when a transition metal, such as copper or zinc, is used as at least a part of the divalent metal atoms of the inorganic domain, the antibacterial/antifungal property can be obtained. The hybrid material of the present invention has a high degree of freedom with respect to the choice of the composition thereof, and hence, excellent antibacterial/antifungal property can be achieved by appropriately combining the above-mentioned raw materials depending on the intended use of the hybrid material.

With respect to the hybrid material of the present invention having antibacterial/antifungal property, in which at least one organic polymer having a cationic functional group and optionally an anionic functional group is used as at least a part of the organic domain, it is preferred to use, as the cationic functional group, a quaternary ammonium salt functional group and/or a functional group having a heterocyclic 6-membered ring structure in which at least one nitrogen atom is present as a hetero atom, from the viewpoint of the ease in the polymer production and the low cost in obtaining the polymer. Further, from the viewpoint of obtaining further improved antibacterial/antifungal property, it is preferred that the cationic functional group content of the organic domain is 5% by weight or more, more preferably 10% by weight or more, still more preferably 20% or more, and it is also preferred that the organic domain is comprised of at least one organic polymer which is composed only of a monomer unit having a cationic functional group.

On the other hand, examples of the above-mentioned "at least one organic polymer having a monomer unit having an antibacterial/antifungal functional group and an anionic functional group" include an organic polymer having an anionic functional group and a haloalkylthio type functional group (as an antibacterial/antifungal functional group) in a main chain or side chain thereof, and an organic polymer having an anionic functional group and an azole derivative functional group (as an antibacterial/antifungal functional group) in a main chain or side chain thereof. Further examples of such polymers include a polymer obtained by chemically bonding a compound which is conventionally known as an antibacterial or antifungal reagent (as an antibacterial/antifungal functional group) to an organic polymer having an anionic functional group. These antibacterial/antifungal functional groups can be used in combination with cationic functional groups. The above-mentioned organic polymer can be appropriately chosen so as to achieve antibacterial/antifungal property suitable for the intended use of the antibacterial/antifungal reagent. Further, a plurality of different organic polymers, each "having a monomer unit having an antibacterial/antifungal functional group and an anionic functional group" can be appropriately used in combination depending on the intended use of the antibacterial/antifungal reagent. Also, an organic polymer having an anionic functional group and at least two different antibacterial/antifungal functional groups can be used. When the above-mentioned "at least one organic polymer having a monomer unit having an antibacterial/antifungal functional group and an anionic functional group" is used, from the viewpoint of obtaining further improved antibacterial/antifungal property, it is preferred that the antibacterial/antifungal functional group content of the organic domain is 5% by weight or more, more preferably 10% or more, still more preferably 20% or more.

Of divalent metal atoms which can be used in the inorganic domain, zinc and copper are advantageous not only in that these metals are not so harmful to the human health, but also in that these metals have high antibacterial/antifungal property. Therefore, these metals are especially advantageous from the viewpoint of obtaining an excellent antibacterial/antifungal reagent.

Further, since the hybrid material of the present invention contains a number of siloxane linkages, further improved antibacterial property can be achieved by incorporating a monovalent metal atom (such as silver) into the hybrid material through a chemical bond.

With respect to the method for using the antibacterial/antifungal hybrid material (an antibacterial/antifungal reagent) of the present invention, there is no particular limitation. Examples of such methods include a method in which the hybrid material is mixed with a cement material (as the inorganic matrix), and the resultant mixture is cured to obtain a cured form of a mixture of the hybrid materiel and the cement material, which cured form is used as a jointing material; a method in which the hybrid material is used in the form of a mixture thereof with a caulking material; a method in which the hybrid material is used in the form of a mixture thereof with a resin; and a method in which the hybrid material is used in the form of a composition thereof with a conventional coating composition, such as a latex, to form a coating.

Of the above methods, especially preferred is a method in which the hybrid material (i.e., the antibacterial/antifungal reagent of the present invention) is used in the form of a mixture thereof with a cement material. The reason for this is as follows. The organic polymer domain of the hybrid material of the present invention forms chemical bonds with the cement material. In addition, the inorganic domain also has an interaction with the cement material. Therefore, the cured form of the mixture of the hybrid material with the cement material can be obtained without causing a lowering of the strength of the cured form. Especially when the antibacterial/antifungal reagent contains calcium atoms as the divalent metal atoms of the inorganic domain, the affinity of the reagent to the cement material becomes high, so that, for example, when the calcium atoms are used in combination with another metal, such as copper or zinc, it becomes possible to obtain excellent cured forms of the mixture of the hybrid material with the cement material, which exhibit further improved antibacterial property.

In the present invention, "the cured form of the mixture of the hybrid material with the cement material can be obtained without causing a lowering of the strength of the cured form" means that even when the strength of the cured form of the mixture of the hybrid material with the cement material is lowered, the degree of lowering is within the range of lowering caused by a change in the specific gravity, and of course, it is possible that the strength does not change at all or the strength is improved.

Further, with respect to the hybrid material of the present invention, for example, a transparent hybrid material can be obtained by controlling of the production conditions and/or choosing the raw materials. For example, the transparent hybrid material can be obtained by the use of magnesium or copper as the divalent atom of the inorganic domain. The transparent hybrid material can be advantageously used alone or in the form of a mixture thereof with a matrix, such as the above-mentioned polymer emulsion, in a field where the formation of a transparent coating is required. For example, the transparent coating or the above-mentioned mixture can be advantageously used to form a coating on a face shield of a motorcycle, a door mirror of a car, a mirror, a pair of goggles and a lens.

When, as mentioned above, the hybrid material or a mixture thereof with a matrix is applied to a substrate, an appropriate substrate can be chosen from various organic or inorganic substrates, such as cured forms of cements, ceramics, glasses, resins, metals and coatings.

Further, the hybrid material of the present invention can be used not only as an additive for a matrix, but also can be used alone as a functional material or can be applied to a cured form of a cement, a ceramic, a glass, a resin, a metal, a coating or the like.

In the present invention, when it becomes necessary to control the size of the hybrid material of the present invention (which is used, for example, as the above-mentioned additive), the size of the hybrid material can be controlled by a method, such as a method in which the size of the hybrid material is controlled by adjusting the chemical conditions, such as pH, or a method in which the size of the hybrid material is controlled by physical means, e.g., by means of a dispersion- or emulsion-forming apparatus (disperser or homogenizer) having a high speed revolution blades. From these methods, an appropriate method can be chosen depending on the desired size of the hybrid material and the like.

When the hybrid material of the present invention is put into practical use after purification (washing), it is preferred to perform the purification by a centrifugation method in which the washing of the hybrid material is performed by repeating the sequence of dilution of the hybrid material with purified water, followed by centrifugal separation, and removal of the supernatant liquid, or a filtration method in which the hybrid material is filtered through a hollow fiber or a filter cloth. When purification is performed by the filtration method, a filter material can be appropriately chosen taking into consideration the particle size of the hybrid material and the particle size of substances to be removed. Further, from the viewpoint of suppression of the clogging of the filter material, it is preferred to employ a method in which the filtration is performed by continuously feeding a liquid containing the hybrid material to a hollow fiber membrane module by means of a pump or a method in which the filtration is performed while appropriately conducting the reverse washing.

In the present invention, by appropriately adjusting the composition of the hybrid material, it is possible not only to obtain the above-mentioned transparent hybrid material, but also to obtain a hybrid material having optical characteristics (e.g., color and refractive index) ascribed to the component elements of the hybrid material. Thus, in the present invention, it is possible to obtain a hybrid material which can be advantageously used as an optical material (e.g., a coating agent for lenses). For example, by using magnesium as the divalent metal atom of the inorganic domain, it becomes possible to obtain an opaque or transparent hybrid material. Similarly, by using copper, it becomes possible to obtain a hybrid material whose color is blue, green or a color therebetween. By using nickel, it becomes possible to obtain a hybrid material having a green color. By using cobalt, it becomes possible to obtain a hybrid material whose color is bluish purple, reddish purple or a color therebetween. Further, by using the hybrid material of the present invention in combination with an electrolyte, a solid or coagulated electrolyte can be obtained. Thus, the hybrid material of the present invention can be used in various application fields.

BEST MODE FOR CARRYING OUT THE INVENTION

Hereinbelow, the present invention will be described in more detail with reference to the following Examples and Comparative Examples, which should not be construed as limiting the scope of the present invention.

In the Examples and Comparative Examples, various properties were measured and evaluated as follows.

(1) The Contact Angle of a Waterdrop Against the Coating:

The contact angle of a waterdrop against the coating was measured by a water drop contact angle measuring system (CA-A, manufactured and sold by KYOWA INTERFACE SCIENCE Co., LTD., Japan), after the coating was dried at 80° C., for 5 minutes and allowed to stand still for 12 hr or more.

(2) The Stain Resistance:

The stain resistance of each of the coatings obtained in the Examples was evaluated as follows. The coatings obtained in the Examples and the below-described comparative coatings 1 and comparative coating 2 were left on the roof of a 4-story building in Fuji-shi, Shizuoka-ken, Japan, for several days, where the coatings were exposed to the raindrops. Then, the coatings were visually observed to evaluate the dirtiness of each of the coatings. Comparative coatings 1 were, respectively, formed from the same polymer emulsions as used in the coatings (each formed from the hydrophilic coating composition of the present invention) obtained in the Examples. (Therefore, specifically, for example, the comparative coating 1 which should be compared with the coating obtained in Example 1 is the coating obtained in Comparative Example 1; the comparative 1 which should be compared with the coating obtained in Example 8 is the coating obtained in Comparative Example 2; and the comparative coating 1 which should be compared with the coating obtained in Example 20 is the coating obtained in Comparative Example 10.) As the comparative coating 2, the coating formed from a commercially available stain resistant coating composition described in Comparative Example 9 was used. The above test was conducted for a period of 1 to 3 months, which period was determined, taking into consideration the seasonal difference in the rainfall. With respect to the criteria of the evaluation, a coating having a dirtiness less than that of the comparative coating 1 was evaluated as "○", and a coating having a dirtiness less than that of the comparative coating 2 (formed from a commercially available coating composition described in Comparative Example 9) was evaluated as "◎".

With respect to the coatings obtained in the Comparative Examples, which were used neither as the above-mentioned comparative coatings 1 nor the above-mentioned comparative coating 2 (i.e., the coatings obtained in Comparative Examples other than Comparative Examples 1, 2, 9 and 10), the evaluation of the stain resistance was conducted in the same manner as mentioned above. (Those coatings obtained in the Comparative Examples were compared with the coatings obtained in Comparative Examples 1 and 2.)

(3) Evaluation of the Antibacterial Property of the Hybrid Material:

The evaluation of the antibacterial property was conducted by the following method. First, a dispersion of a sample, which has a predetermined concentration (weight/volume %) of the sample, was prepared using a sterilized, purified water. Next, Mueller Hinton Agar (manufactured and sold by Difco Laboratories, U.S.A.) was sterilized, and dissolved into water. Then, the resultant solution was kept at a temperature of from 50° C. to 60° C. Into the solution was added a predetermined amount of the above-mentioned dispersion, and the resultant was mixed thoroughly. Then, the resultant mixture was distributed into petri dishes, followed by solidification, to thereby obtain test plates. Separately, a subcultured test bacteria (E coli: Escherichia coli IFO 3972) was inoculated into Mueller Hinton Agar (manufactured and sold by Difco Laboratories, U.S.A.) and incubated at 35±1° C. for 18 hr to 20 hr. After the incubation, the amount of bacteria was adjusted to $10^6$/ml by dilution with the above culture medium to obtain a bacteria liquid and this liquid was used as a bacteria inoculation liquid. This bacteria inoculation liquid was streak-coated on each of the above-mentioned test plates (streak length=about 1 to 2 cm) by a resin loop (inner diameter=about 1 mm), followed by incubation at 35±1° C. for from 18 hr to 20 hr. After the incubation, the growth of the test bacteria was visually observed.

(4) X-Ray Diffraction Analysis:

The X-ray diffraction analysis was conducted by means of an X-ray diffractometer (RINT-2500, manufactured and sold by Rigaku Corporation, Japan) under the following the conditions: radiation source: CuKa, scanning axis: 2θ/θ, step interval: 0.02°, scanning speed: 4.0°/min, acceleration voltage: 40 kV, acceleration current: 200 mA, and the half width was obtained by stripping Ka2 from the obtained diffraction line.

(5) Solid $^{29}$SiNMR Analysis:

The solid $^{29}$SiNMR analysis was conducted by means of DSX-400 (manufactured and sold by Bruker Instruments Inc., Germany) under the following conditions: observation frequency: 79.5 MHz, DD/MAS mode, revolution rate: 4900 Hz, pulse width: 6.0 μsec (45°), waiting time: 30 sec, temperature: room temperature, an integrated value obtained from the data of 100 cycles of the analysis was used.

(6) Organic Domain/Inorganic Domain Weight Ratio:

In each of Examples 23 to 28, 30 and 31, the organic domain had an anionic functional group, so that the organic domain/inorganic domain weight ratio was determined.

For the determination of the organic domain/inorganic domain weight ratio of the hybrid material, a calibration curve was prepared as follows. First, several samples of the hybrid material were prepared, and each of the prepared samples was subjected to the following treatment. The sample hybrid material was washed with the same solvent as used in the production of the sample hybrid material in an amount which is at least about 100 times the total weight of the raw materials (in terms of solids) of the sample hybrid material until the difference in dry weight between the sample hybrid material before washing and the sample hybrid material after washing became 10% or less. Then, the sample hybrid material was subjected to drying at 60° C. under a reduced pressure of 1 kPa or less for more than 5 hours until the weight of the hybrid material became constant (i.e., the change in weight of the sample hybrid material became 0.5% or less per hour).

With respect to the dried sample hybrid material, the weights of the organic domain and the inorganic domain were determined as follows. By X-ray fluorescence spectrometry, the weights of the silicon atom, the divalent metal atom and the aluminum atom were determined in terms of the weights of oxides thereof, and the total weight of the silicon oxide, the divalent metal oxide and the aluminum oxide was defined as the weight of the inorganic domain. Separately, the sample hybrid material was heated in air by using an electric furnace to elevate the temperature of the sample hybrid material from room temperature to 1,000° C. at a rate of 25° C./min, followed by maintaining the temperature at 1,000° C. for 10 minutes, to thereby calcine the sample hybrid material. The resultant ash was analyzed by various elemental analyses.

From the results of the X-ray fluorescence spectrometry and the decrease in weight of the sample hybrid material which was caused by the calcination, the weight of the organic domain was obtained. From the obtained weights of the organic domain and the inorganic domain, the organic domain/inorganic domain weight ratio of the sample hybrid material was obtained. Further, the sample hybrid material was subjected to infrared spectroscopy to obtain the ratio (peak intensity ratio) of the intensity of the absorbance peak ascribed to the carbonyl moiety of a carboxylic acid group of the organic domain to the intensity of the absorbance peak ascribed to an —O—Si—O— linkage of the inorganic domain. Based on the relationship between the organic domain/inorganic domain weight ratios of the samples and the peak intensity ratios of the samples, a calibration curve was prepared.

With respect to the hybrid material, the organic domain/inorganic domain weight ratio thereof was obtained by infrared spectroscopy, using the obtained calibration curve. Specifically, the hybrid material was subjected to the above-mentioned infrared spectroscopy to obtain a peak intensity ratio as defined above. From the results of the infrared spectroscopy, the organic domain/inorganic domain weight ratio of the hybrid material was obtained using the above-mentioned calibration curve.

(7) The Washing Operation:

In each of the Examples and Comparative Examples, the produced material was subjected to the below-mentioned "Washing step 1" (the first washing operation), followed by the below-mentioned "Washing step 2" (the further washing operation) which was repeated a predetermined number of times.

Washing step 1: The dispersion of the obtained material was diluted 5 times (by weight) with purified water to obtain a diluted dispersion, and the dispersion was centrifuged, followed by removal of the supernatant liquid.

Washing step 2: Purified water was charged into the sediment obtained in washing step 1 so that the total weight of the sediment and purified water became the same as that of the above-mentioned diluted dispersion, thereby redispersing the sediment. The resultant dispersion was centrifuged in the same manner as in the above-mentioned washing step 1, followed by removal of the supernatant liquid.

(8) Various Operations in the Example and Comparative Example were Conducted at Room Temperature unless Otherwise Indicated.

EXAMPLE 1

(1) Synthesis of a Hydrophilicity Reagent 2.5 Parts by weight of a 20% by weight aqueous solution of polydiallyldimethylammonium chloride (reagent manufactured and sold by Aldrich, Ltd., U.S.A.; weight average molecular weight=100,000 to 200,000) and 5 parts by weight of a 10% by weight aqueous solution of sodium metasilicate nonahydrate were mixed together and the resultant mixture was stirred for 10 minutes. Then, into the mixture were charged 3 parts by weight of a 10% by weight aqueous solution of calcium nitrate tetrahydrate and 0.33 parts by weight of 1 N hydrochloric acid to obtain an opaque hydrophilicity reagent dispersion A. The obtained hydrophilicity reagent dispersion A was subjected to a washing operation comprising the above-mentioned washing step 1 using a centrifuge (Centra MP 4 type, manufactured and sold by International Equipment Company, U.S.A.) and the subsequent washing step 2 (which was repeated 3 times in total). The resultant was dried at 60° C. under a reduced pressure of 1 kPa for not less than 8 hr, and then, analyzed by infra-red spectroscopy. In the analysis, an absorption ascribed to an organic component and an absorption ascribed to a siloxane linkage (a shifted absorption) were observed, respectively, at 2930 $cm^{-1}$ and 970 $cm^{-1}$, thereby confirming the presence of a particle composed of a hybrid of the organic domain and the inorganic domain (as mentioned above, when calcium is bonded to siloxane, the wavelength at which an absorption ascribed to the siloxane is observed is shifted to 970 $cm^{-1}$.)

(2) Preparation and Evaluation of a Hydrophilic Coating Composition

3 Parts by weight of an acryl latex (E901, manufactured and sold by Asahi Kasei Kabushiki Kaisha, Japan; solids content: 55% by weight) and 2 parts by weight of the hydrophilicity reagent dispersion A were mixed together and the resultant mixture was stirred for 30 minutes to obtain a hydrophilic coating composition. The obtained composition was applied to the surface of an aluminum substrate which had been subjected to anodic oxidation using wire bar #16, followed by drying at 80° C. for 5 minutes. Then, the resultant aluminum substrate was allowed to stand at room temperature for 12 hours to obtain a dried coating formed on the aluminum substrate. With respect to the obtained dried coating, the contact angle of a waterdrop against the surface of the coating was measured and found to be 54°. Separately from the measurement of the contact angle, about 30 mg of a waterdrop was put on the dried coating and the coating was allowed to stand for 1 minute. Subsequently, the aluminum substrate having the coating formed thereon was raised to stand vertically. As a result, it was found that the waterdrop flowed down swiftly on the coating and there was no residue on the coating after the coating was dried. The release of the coating from the substrate was not observed. Further, with respect to the coating, the above-mentioned test for evaluating the stain resistance was conducted for 2 months, and it was found that the stain resistance of the coating was ○. In addition, the storage stability of the above-mentioned hydrophilic coating composition (coating liquid) was evaluated as follows. The coating liquid was placed in a glass bottle, and the bottle was sealed tightly and stored at room temperature. Even after the bottle containing the coating liquid had been stored for 1 week, the coating liquid maintained its fluidity and was usable as a coating liquid.

EXAMPLE 2

A hydrophilic coating composition was produced in substantially the same manner as in Example 1, except that the amount of the hydrophilicity reagent dispersion A was changed to 1 part by weight. The coating formation and evaluations were conducted in the same manner as in Example 1. The contact angle of a waterdrop was measured and found to be 57°. A waterdrop flowed down swiftly on the coating, and there was no residue on the coating after the coating was dried. The release of the coating from the substrate was not observed. Further, with respect to coating, the above-mentioned test for evaluating the stain resistance was conducted for 2 months, and it was found that the stain resistance of the coating was ○. In addition, the coating liquid was stored under the same conditions as in Example 1. Even after the bottle containing the coating liquid had been stored for 1 week or more, the coating liquid maintained its fluidity and was usable as a coating liquid.

EXAMPLE 3

(1) Synthesis of a Hybrid Material

A blue hybrid material dispersion B was produced in substantially the same manner as in Example 1, except that, instead of a 10% by weight aqueous solution of calcium nitrate tetrahydrate, a 10.6% by weight aqueous solution of copper sulfate pentahydrate was used. The hybrid material dispersion B was subjected to washing operations and drying operations in substantially the same manner as in Example 1 to thereby obtain a final dried hybrid material. The final dried hybrid material was analyzed by infra-red spectroscopy. In the analysis, both a peak ascribed to an organic compound and a peak ascribed to an inorganic compound were observed, thereby confirming the presence of the hybrid material of the present invention in the hybrid material dispersion B.

(2) Preparation and Evaluation of a Hydrophilic Coating Composition

3 Parts by weight of an acryl latex (E901, manufactured and sold by Asahi Kasei Kabushiki Kaisha, Japan; solids content: 55% by weight) and 2 parts by weight of the hybrid material dispersion B were mixed together, and the resultant mixture was stirred for 30 minutes to obtain a hydrophilic coating composition. The obtained composition was applied to the surface of an aluminum substrate which had been subjected to anodic oxidation using wire bar #16, followed by drying at 80° C. for 5 minutes. Then, the resultant aluminum substrate was allowed to stand at room temperature for 12 hours to obtain a dried coating formed on the aluminum substrate. With respect to the obtained dried coating, the contact angle of a waterdrop against the surface of the coating was measured and found to be 56°. Separately from the measurement of the contact angle, about 30 mg of a waterdrop was put on the dried coating and the coating was allowed to stand for 1 minute. Subsequently, the aluminum substrate having the coating formed thereon was raised to stand vertically. As a result, it was found that the waterdrop flowed down swiftly on the coating and there was no residue on the coating after the coating was dried. The release of the coating from the substrate was not observed. Further, the coating liquid was stored under the same conditions as in Example 1. Even after the bottle containing the coating liquid had been stored for 1 week or more, the coating liquid maintained its fluidity and was usable as a coating liquid.

EXAMPLE 4

(1) Synthesis of a Hybrid Material

An opaque hybrid material dispersion C was produced in substantially the same manner as in Example 3, except that, instead of a 10.6% by weight aqueous solution of copper sulfate pentahydrate, a 12.2% by weight aqueous solution of zinc sulfate heptahydrate was used. The hybrid material dispersion C was subjected to washing operations and drying operations in substantially the same manner as in Example 1 to thereby obtain a final dried hybrid material. The final dried hybrid material was analyzed in the same manner as in Example 3. As a result, it was confirmed that the hybrid material of the present invention was present in the hybrid material dispersion C.

(2) Preparation and Evaluation of a Hydrophilic Coating Composition

A hydrophilic coating composition was produced in substantially the same manner as in Example 3, except that the hybrid material dispersion B was changed to the hybrid material dispersion C. The coating formation and evaluations were conducted in the same manner as in Example 3. The contact angle of a waterdrop against the surface of the coating was measured and found to be 55°. The waterdrop flowed down swiftly on the coating, and there was no residue after the coating was dried. The release of the coating from the substrate was not observed. Further, the coating liquid was stored under the same conditions as in Example 1. Even after the bottle containing the coating liquid had been stored for 1 week or more, the coating liquid maintained its fluidity and was usable as a coating liquid.

EXAMPLE 5

(1) Synthesis of a Hydrophilicity Reagent

An opaque hydrophilicity reagent dispersion D was produced in substantially the same manner as in Example 1, except that the amount of a 20% by weight aqueous solution of polydiallyldimethylammonium chloride (reagent, manufactured and sold by Aldrich, Ltd., U.S.A.; weight average molecular weight=100,000 to 200,000) was changed to 0.6 parts by weight. The dispersion D was subjected to washing operations and drying operations in substantially the same manner as in Example 1 to thereby obtain a final dried hybrid material. The final dried hybrid material was analyzed in the same manner as in Example 1. As a result, it was confirmed that the hydrophilicity reagent of the present invention was present in the hydrophilicity reagent dispersion D.

(2) Preparation and Evaluation of a Hydrophilic Coating Composition

A hydrophilic coating composition was produced in substantially the same manner as in Example 2, except that the hybrid material dispersion A was changed to the hybrid material dispersion D. The coating formation and evaluations were conducted in the same manner as in Example 1. The contact angle of a waterdrop against the surface of the coating was measured and found to be 53°. The waterdrop flowed down swiftly on the coating, and there was no residue on the coating after the coating was dried. The release of the coating from the substrate was not observed. Further, the coating liquid was stored under the same conditions as in Example 1. Even after the bottle containing the coating liquid for 1 week or more, the coating liquid maintained its fluidity and was usable as a coating liquid.

EXAMPLE 6

(1) Synthesis of a Hybrid Material 0.6 Parts by weight of a 20% by weight aqueous solution of polydiallyldimethylammonium chloride (reagent, manufactured and sold by Aldrich, Ltd., U.S.A.; weight average molecular weight=100,000 to 200,000) and 5 parts by weight of a 10% by weight aqueous solution of sodium metasilicate nonahydrate were mixed together and the resultant mixture was stirred for 10 minutes. Then, into the mixture were charged 3 parts by weight of a 10.8% by weight aqueous solution of magnesium nitrate hexahydrate and 0.33 parts by weight of 1 N hydrochloric acid to obtain an opaque hybrid material dispersion E. The hybrid material dispersion E was subjected to washing operations and drying operations in substantially the same manner as in Example 1 to thereby obtain a final dried hybrid material. The final dried hybrid material was analyzed in the same manner as in Example 3. As a result, it was confirmed that the hybrid material of the present invention was present in the hybrid material dispersion E. The hybrid material was analyzed by X-ray diffractometry and it was found that the hybrid material was amorphous at $2\theta=15°$ to $55°$. Further, the hybrid material was analyzed by $^{29}$SiNMR and it was found that $(Q1+Q2)/(Q3+Q4)=1.4$ (2) Preparation and Evaluation of a Hydrophilic Coating Composition A hydrophilic coating composition was produced in substantially the same manner as in Example 3, except that the hybrid material dispersion B was changed to the hybrid material dispersion E. The coating formation and evaluations were conducted in the same manner as in Example 3. The contact angle of a waterdrop against the surface of the coating was measured and found to be 50°. The waterdrop flowed down swiftly on the coating, and there was no residue on the coating after the coating was dried. The release of the coating from the substrate was not observed. Further, with respect to the coating, the above-mentioned test for evaluating the stain resistance was conducted for 2 months, and it was found that the stain resistance of the coating was ◯. In addition, the coating liquid was stored under the same conditions as in Example 1. Even after the bottle containing the coating liquid had been stored for 1 week or more, the coating liquid maintained its fluidity and was usable as a coating liquid.

EXAMPLE 7

A hydrophilic coating composition was produced in substantially the same manner as in Example 6, except that the amount of the hybrid material dispersion E was changed to 1 part by weight. The coating formation and evaluations were conducted in the same manner as in Example 3. The contact angle of a waterdrop against the surface of the coating was measured and found to be 51°. The waterdrop flowed down swiftly on the coating, and there was no residue after the coating was dried. The release of the coating from the substrate was not observed. Further, with respect to the coating, the above-mentioned test for evaluating the stain resistance was conducted for 2 months, and it was found that the stain resistance of the coating was ◯. In addition, the coating liquid was stored under the same conditions as in Example 1. Even after 1 week or more, the coating liquid maintained its fluidity and was usable as a coating liquid.

EXAMPLE 8

A hydrophilic coating composition was produced in substantially the same manner as in Example 6, except that the acryl latex was changed to E316 manufactured and sold by Asahi Kasei Kabushiki Kaisha, Japan (solids content: 45% by weight). The coating formation and evaluations were conducted in the same manner as in Example 3. The contact angle against the surface of the coating was measured and found to be 60°. There was no residue after the coating, on which a waterdrop had been put, was dried. The release of the coating from the substrate was not observed. Further, with respect to the coating, the above-mentioned test for evaluating the stain resistance was conducted for 2 months, and it was found that the stain resistance of the coating was ⊚. Further, the coating liquid was stored under the same conditions as in Example 1. Even after the bottle containing the coating liquid had been stored for 1 week or more, the coating liquid maintained its fluidity and was usable as a coating liquid.

EXAMPLE 9

A hydrophilic coating composition was produced in substantially the same manner as in Example 8, except that the amount of the hybrid material dispersion E was changed to 3 parts by weight. The coating formation and evaluations were conducted in the same manner as in Example 3. The contact angle of a waterdrop against the surface of the coating was measured and found to be 57°. There was no residue, on the coating after the coating on which a waterdrop had been put, was dried. The release of the coating from the substrate was not observed. Further, with respect to the coating, the above-mentioned test for evaluating the stain resistance was conducted for 2 months, and it was found that the stain resistance of the coating was ⊚. In addition, the coating liquid was stored under the same conditions as in Example 1. Even after 1 week or more, the coating liquid maintained its fluidity and was usable as a coating liquid.

EXAMPLE 10

(1) Synthesis of a Hybrid Material

An opaque hybrid material dispersion F was produced in substantially the same manner as in Example 6, except that, instead of a 10.8% by weight aqueous solution of magnesium nitrate hexahydrate, a 9.7% by weight aqueous solution of strontium nitrate was used. The hybrid material dispersion F was subjected to washing operations and drying operations in substantially the same manner as in Example 6 to thereby obtain a final dried hybrid material. The final dried hybrid material was analyzed in the same manner as in Example 3. As a result, it was confirmed that the hybrid material of the present invention was present in the hybrid material dispersion F. Further, the hybrid material was analyzed by $^{29}$SiNMR, and it was found that neither a Q3 nor a Q4 peak was observed and only Q1 and Q2 peaks were observed.

(2) Preparation and Evaluation of a Hydrophilic Coating Composition

A hydrophilic coating composition was produced in substantially the same manner as in Example 3, except that the hybrid material dispersion B was changed to the hybrid material dispersion F. The coating formation and evaluations were conducted in the same manner as in Example 3. The contact angle of a waterdrop against the surface of the coating was measured and found to be 47°. The waterdrop flowed down swiftly and there was no residue on the coating after the coating was dried. The release of the coating from the substrate was not observed. Further, with respect to the coating, the above-mentioned test for evaluating the stain resistance was conducted for 2 months, and it was found that the stain resistance of the coating was ◯. In addition, the coating liquid was stored under the same conditions as in Example 1. Even after the bottle containing the coating liquid had been stored for 1 week or more, the coating liquid maintained its fluidity and was usable as a coating liquid.

EXAMPLE 11

A hydrophilic coating composition was produced in substantially the same manner as in Example 10, except that the amount of the hybrid material dispersion F was changed to 1 part by weight. The coating formation and evaluations were conducted in the same manner as in Example 3. The contact angle of a waterdrop against the surface of the coating was measured and found to be 51°. The waterdrop flowed down swiftly and there was no residue after the coating was dried. The release of the coating from the substrate was not observed. Further, with respect to the coating, the above-mentioned test for evaluating the stain resistance was conducted for 2 months, and it was found that the stain resistance of the coating was ◯. In addition, the coating liquid was stored under the same conditions as in Example 1. Even after the bottle containing the coating liquid had been stored for 1 week, the coating liquid maintained its fluidity and was usable as a coating liquid.

EXAMPLE 12

A hydrophilic coating composition was produced in substantially the same manner as in Example 9, except that the hybrid material dispersion E was changed to the hybrid material dispersion F. The coating formation and evaluations were conducted in the same manner as in Example 3. The contact angle of a waterdrop against the surface of the coating was measured and found to be 52°. The waterdrop flowed down swiftly and there was no residue after the coating was dried. The release of the coating from the substrate was not observed. Further, with respect to the coating, the above-mentioned test for evaluating the stain resistance was conducted for 2 months, and it was found that the stain resistance of the coating was ⊚. In addition, the coating liquid was stored under the same conditions as in Example 1. Even after the bottle containing the coating liquid had been stored for 1 week or more, the coating liquid maintained its fluidity and was usable as a coating liquid.

EXAMPLE 13

(1) Synthesis of a Hybrid Material

An opaque hybrid material dispersion G was produced in substantially the same manner as in Example 6, except that, instead of a 10.8% by weight aqueous solution of magnesium nitrate hexahydrate, a 12.2% by weight aqueous solution of zinc sulfate heptahydrate was used. The hybrid material dispersion G was subjected to washing operations and drying operations in substantially the same manner as in Example 1 to thereby obtain a final dried hybrid material. The final dried hybrid material was analyzed in the same manner as in Example 3. As a result, it was confirmed that the hybrid material of the present invention was present in the hybrid material dispersion G.

(2) Preparation and Evaluation of a Hydrophilic Coating Composition

A hydrophilic coating composition was produced in substantially the same manner as in Example 3, except that the hybrid material dispersion B was changed to the hybrid material dispersion G. The coating formation and evaluations were conducted in the same manner as in Example 3. The contact angle of a waterdrop against the surface of the coating was measured and found to be 59°. The waterdrop flowed down swiftly on the coating and there was no residue on the coating after the coating was dried. The release of the coating from the substrate was not observed. Further, the coating liquid was stored under the same conditions as in Example 1. Even after the bottle containing the coating liquid had been stored for 1 week or more, the coating liquid maintained its fluidity and was usable as a coating liquid.

EXAMPLE 14

(1) Synthesis of a Hydrophilicity Reagent 0.6 Parts by weight of a 20% by weight aqueous solution of polydiallyldimethylammonium chloride (reagent manufactured and sold by Aldrich, Ltd., U.S.A.; weight average molecular weight=100,000 to 200,000) and 3 parts by weight of a 10% by weight aqueous solution of calcium nitrate tetrahydrate were mixed together and the resultant mixture was stirred for 10 minutes. Then, into the mixture were charged 5 parts by weight of a 2.1% by weight colloidal silica (reagent LUDOX SM30, manufactured and sold by Aldrich, Ltd., U.S.A.) to obtain an opaque hydrophilicity reagent dispersion H. The dispersion H was subjected to washing operations and drying operations in substantially the same manner as in Example 1 to thereby obtain a final dried hybrid material. The final dried hybrid material was analyzed in the same manner as in Example 1. As a result, it was confirmed that the hydrophilicity reagent of the present invention was present in the hydrophilicity reagent dispersion H.

(2) Preparation and Evaluation of a Hydrophilic Coating Composition

A hydrophilic coating composition was produced in substantially the same manner as in Example 1, except that the hydrophilicity reagent dispersion A was changed to the hydrophilicity reagent dispersion H. The coating formation and evaluations were conducted in the same manner as in Example 1. The contact angle of a waterdrop against the surface of the coating was measured and found to be 54°. The waterdrop flowed down swiftly and there was no residue on the coating after the coating was dried. The release of the coating from the substrate was not observed. Further, the coating liquid was stored under the same conditions as in Example 1. Even after the bottle containing the coating liquid had been stored for 1 week or more, the coating liquid maintained its fluidity and was usable as a coating liquid.

EXAMPLE 15

A hydrophilic coating composition was produced in substantially the same manner as in Example 8, except that the hybrid material dispersion E was changed to the hydrophilicity reagent dispersion H. The coating formation and evaluations were conducted in the same manner as in Example 1. The contact angle of a waterdrop against the surface of the coating was measured and found to be 59°. There was no residue after the coating was dried. The release of the coating from the substrate was not observed. Further, the coating liquid was stored under the same conditions as in Example 1. Even after the bottle containing the coating liquid had been stored for 1 week or more, the coating liquid maintained its fluidity and was usable as a coating liquid.

EXAMPLE 16

(1) Synthesis of a Hybrid Material 0.6 Parts by weight of a 20% by weight aqueous solution of polydiallyldimethylammonium chloride (reagent, manufactured and sold by Aldrich, Ltd., U.S.A.; weight average molecular weight=100,000 to 200,000) and 3 parts by weight of a 12.2% by weight aqueous solution of zinc sulfate heptahydrate were mixed together and the resultant mixture was stirred for 10 minutes. Then, into the mixture were charged 5 parts by weight of a 2.1% by weight colloidal silica (LUDOX SM30, manufactured and sold by Aldrich, Ltd., U.S.A.) to obtain an opaque hybrid material dispersion I. The hybrid material dispersion I was subjected to washing operations and drying operations in substantially the same manner as in Example 1 to thereby obtain a final dried hybrid material. The final dried hybrid material was analyzed in the same manner as in Example 3. As a result, it was confirmed that the hybrid material of the present invention was present in the hybrid material dispersion I.

(2) Preparation and Evaluation of a Hydrophilic Coating Composition

A hydrophilic coating composition was produced in substantially the same manner as in Example 3, except that the hybrid material dispersion B was changed to the hybrid material dispersion I. The coating formation and evaluations were conducted in the same manner as in Example 3. The contact angle of a waterdrop against the surface of the coating was measured and found to be 60°. The waterdrop flowed down swiftly on the coating and there was no residue on the coating after the coating was dried. The release of the coating from the substrate was not observed. Further, the coating liquid was stored under the same conditions as in Example 1. Even after the bottle containing the coating liquid had been stored for 1 week or more, the coating liquid maintained its fluidity and was usable as a coating liquid.

EXAMPLE 17

(1) Synthesis of a Hybrid Material

A hybrid material dispersion J was produced in substantially the same manner as in Example 16, except that 2.5 parts by weight of a 20% by weight aqueous solution of polydiallyldimethylammonium chloride (reagent manufactured and sold by Aldrich, Ltd., U.S.A.; weight average molecular weight=100,000 to 200,000) was used. The hybrid material dispersion J was subjected to washing operations and drying operations in substantially the same manner as in Example 1 to thereby obtain a final dried hybrid material. The final dried hybrid material was analyzed in the same manner as in Example 3. As a result, it was confirmed that the hybrid material of the present invention was present in the hybrid material dispersion J.

(2) Preparation and Evaluation of a Hydrophilic Coating Composition

A hydrophilic coating composition was produced in substantially the same manner as in Example 7, except that the hybrid material dispersion E was changed to the hybrid material dispersion J. The coating formation and evaluations were conducted in the same manner as in Example 3. The contact angle of a waterdrop against the surface of the coating was measured and found to be 55°. The waterdrop flowed down swiftly on the coating and there was no residue on the coating after the coating was dried. The release of the coating from the substrate was not observed. Further, the coating liquid was stored under the same conditions as in Example 1. Even after the bottle containing the coating liquid had been stored for 1 week or more, the coating liquid maintained its fluidity and was usable as a coating liquid.

EXAMPLE 18

A hydrophilic coating composition was produced in substantially the same manner as in Example 10, except that 0.3 parts of calcium carbonate was further added as a white pigment. The coating formation and evaluations were conducted in the same manner as in Example 3. The contact angle of a waterdrop against the surface of the coating was measured and found to be 44°. The waterdrop flowed down swiftly and there was no residue on the coating after the coating was dried. The release of the coating from the substrate was not observed. Further, the coating liquid was stored under the same conditions as in Example 1. Even after the bottle containing the coating liquid had been stored for 1 week or more, the coating liquid maintained its fluidity and was usable as a coating liquid.

EXAMPLE 19

(1) Synthesis of a Hybrid Material

A hybrid material dispersion K was produced in substantially the same manner as in Example 6, except that, instead of 1 N hydrochloric acid, a 4% by weight aqueous solution of sodium hydroxide was used. The hybrid material dispersion K was subjected to washing operations and drying operations in substantially the same manner as in Example 1 to thereby obtain a final dried hybrid material. The final dried hybrid material was analyzed in the same manner as in Example 3. As a result, it was confirmed that the hybrid material of the present invention was present in the hybrid material dispersion K. The hybrid material was analyzed by X-ray diffractometry and it was found that the hybrid material is amorphous at 2 θ=from 15° to 55°. Further, the hybrid material was analyzed by $^{29}$SiNMR and it was found that $(Q1+Q2)/(Q3+Q4)=1.7$ (2) Preparation and Evaluation of a Hydrophilic Coating Composition A hydrophilic coating composition was produced in substantially the same manner as in Example 9, except that the hybrid material dispersion E was changed to the hybrid material dispersion K. The coating formation and evaluations were conducted in the same manner as in Example 3. The contact angle of a waterdrop against the surface of the coating was measured and found to be 55°. There was no residue after the coating on which a waterdrop had been put was dried. The release of the coating from the substrate was not observed. Further, with respect to the coating, the above-mentioned test for evaluating the stain resistance was conducted for 2 months, and it was found that the stain resistance of the coating was ⊙. In addition, the coating liquid was stored under the same conditions as in Example 1. Even after the bottle containing the coating liquid had been stored for 1 week or more, the coating liquid maintained its fluidity and was usable as a coating liquid.

EXAMPLE 20

(1) Preparation of a Polymer Emulsion Containing a Pigment 309.7 Parts by weight of purified water, 700 parts by weight of titanium oxide (Tipaque CR-97, manufactured and sold by Ishiwara Sangyou Kaisha, Ltd., Japan), 11.2 parts by weight of dispersion reagent (MD20, manufactured and sold by BASF Japan, Ltd., Japan), 49 parts by weight of propyleneglycol and 6 parts by weight of defoaming reagent (SN-Defoamer 382, SAN NOPCO LIMITED, Japan) were mixed together to prepare a pigment paste in which 65% by weight titanium oxide was dispersed. Then, 108.7 parts of an acryl latex (E316, manufactured and sold by Asahi Kaseki Kabushiki Kaisha, Japan; solids content: 45% by weight), 10 parts a 50% by weight aqueous solution of butyl cellosolve which had been prepared in advance by dilution with purified water, 10 parts of 2,2,4-trimethyl-1,3-pentadiolemonoisobutylate (CS-12, manufactured and sold by CHISSO Corporation, Japan) and 51.3 parts of the pigment paste were mixed together to prepare a polymer emulsion containing a pigment.

(2) Preparation and Evaluation of a Hydrophilic Coating Composition

3 Parts by weight of the polymer emulsion which was prepared in process (1) and 1.83 parts by weight of the hybrid material dispersion K were mixed together to produce a hydrophilic coating composition. The coating formation and evaluations were conducted in the same manner as in Example 3. The contact angle of a waterdrop against the surface of the coating was measured and found to be 58°. When a waterdrop was put on the coating, the release of the coating from the substrate was not observed. Further, with respect to the coating, the above-mentioned test for evaluating the stain resistance was conducted for 2 months, and it was found that the stain resistance of the coating was ○. In addition, the coating liquid was stored under the same conditions as in Example 1. Even after the bottle containing the coating liquid had been stored for 1 week or more, the coating liquid maintained its fluidity and was usable as a coating liquid.

EXAMPLE 21

(1) Synthesis of a Hybrid Material

A hybrid material dispersion L was produced in substantially the same manner as in Example 19, except that the amount of a 4% by weight aqueous solution of sodium hydroxide was changed to 1 part by weight. The hybrid material dispersion L was subjected to washing operations and drying operations in substantially the same manner as in Example 1 to thereby obtain a final dried hybrid material. The final dried hybrid material was analyzed in the same manner as in Example 3. As a result, it was confirmed that the hybrid material of the present invention was present in the hybrid material dispersion L. Also, the hybrid material was analyzed by X-ray diffractometry and it was found that the hybrid material was amorphous at 2 θ=from 15° to 55°. Further, the hybrid material was analyzed by $^{29}$SiNMR and it was found that $(Q1+Q2)/(Q3+Q4)=2.1$ (2) Preparation and Evaluation of a Hydrophilic Coating Composition 3 Parts by weight of the polymer emulsion which was prepared in process (1) of Example 20 and 1.83 parts by weight of the hybrid material dispersion L were mixed together to produce a hydrophilic coating composition. The coating formation and evaluations were conducted in the same manner as in Example 3. The contact angle of a waterdrop against the surface of the coating was measured and found to be 59°. When the waterdrop was put on the coating, the release of the coating from the substrate was not observed. Further, with respect to the coating, the above-mentioned test for evaluating the stain resistance was conducted for 2 months, and it was found that the stain resistance of the coating was ○. In addition, the coating liquid was stored under the same conditions as in Example 1. Even after the bottle containing the coating liquid had been stored for 1 week or more, the coating liquid maintained its fluidity and was usable as a coating liquid.

EXAMPLE 22

(1) Synthesis of a Hybrid Material

An opaque hybrid material dispersion M was produced in substantially the same manner as in Example 19, except that, instead of a 10.8% by weight aqueous solution of magnesium nitrate hexahydrate, a 9.7% by weight aqueous solution of strontium nitrate was used. The hybrid material dispersion M was subjected to washing operations and drying operations in substantially the same manner as in Example 1 to thereby obtain a final dried hybrid material. The final dried hybrid material was analyzed in the same manner as in Example 3. As a result, it was confirmed that the hybrid material of the present invention was present in the hybrid material dispersion M. Further, the hybrid material was analyzed by $^{29}$SiNMR, and it was found that neither a Q3 nor a Q4 peak was observed and only Q1 and Q2 peaks were observed.

(2) Preparation and Evaluation of a Hydrophilic Coating Composition

A hydrophilic coating composition was produced in substantially the same manner as in Example 9, except that the hybrid material dispersion E was changed to the hybrid material dispersion M. The coating formation and evaluations were conducted in the same manner as in Example 3. The contact angle of a waterdrop against the surface of the coating was measured and found to be 54°. When a waterdrop was put on the coating, the release of the coating from the substrate was not observed. Further, with respect to the coating, the above-mentioned test for evaluating the stain resistance was conducted for 2 months, and it was found that the stain resistance of the coating was ⊙. In addition, the coating liquid was stored under the same conditions as in Example 1. Even after the bottle containing the coating liquid had been stored for 1 week or more, the coating liquid maintained its fluidity and was usable as a coating liquid.

EXAMPLE 23

(1) Synthesis of a Hybrid Material

To 3 parts by weight of a 10% by weight aqueous solution of polyacrylic acid (reagent, manufactured and sold by Polysciences Inc., U.S.A.; weight average molecular weight: 90,000) were added, in this order, 1.68 parts by weight of a 10% by weight aqueous solution of sodium hydroxide and 2.37 parts by weight of a 10% by weight aqueous solution of sodium metasilicate nonahydrate. The resultant mixture was stirred for 10 minutes, followed by addition of 2.85 parts by weight of a 10.8% by weight aqueous solution of magnesium nitrate hexahydrate which had separately been prepared to obtain an opaque hybrid material dispersion AA. The obtained hybrid material dispersion AA was subjected to a washing operation comprising the above-mentioned washing step 1 using a centrifuge (Centra MP 4 type, manufactured and sold by International Equipment Company, U.S.A.) and the subsequent washing step 2 (which was repeated 3 times in total). The resultant material was dried at 60° C. under a reduced pressure of 1 kPa for not less than 8 hr, and then, analyzed by infra-red spectroscopy. In the analysis, an absorption ascribed to an organic component and an absorption ascribed to a siloxane linkage (a shifted absorption) were observed, and it was confirmed that the hybrid material of the present invention was present in the hybrid material dispersion AA. The weight ratio organic domain/inorganic domain was measured and found to be less than 1.0.

(2) Preparation and Evaluation of a Hydrophilic Coating Composition

3 Parts by weight of an acryl latex (E901, manufactured and sold by Asahi Kasei Kabushiki Kaisha, Japan; solids content: 55% by weight) and 2 parts by weight of the hybrid material dispersion AA were mixed together and the resultant mixture was stirred for 30 minutes to obtain a hydrophilic coating composition. The obtained composition was applied to the surface of an aluminum substrate which had been subjected to anodic oxidation using wire bar #16, followed by drying at 80° C. for 5 minutes. Then, the resultant aluminum substrate was allowed to stand at room temperature for 12 hours to obtain a dried coating formed on the aluminum substrate. With respect to the obtained dried coating, the contact angle of a waterdrop against the surface of the coating was measured and found to be 59°. Separately from the measurement of the contact angle, about 30 mg of a waterdrop was put on the dried coating and the coating was allowed to stand for 1 minute. Subsequently, the aluminum substrate having the coating formed thereon was raised to stand vertically. As a result, it was found that the waterdrop flowed down swiftly on the coating and there was no residue on the coating after the coating was dried. The release of the coating from the substrate was not observed. Further, with respect to the coating, the above-mentioned test for evaluating the stain resistance was conducted for 2 months, and it was found that the stain resistance of the coating was ○. In addition, the storage stability of the above-mentioned hydrophilic coating composition (coating liquid) was evaluated as follows. The coating liquid was placed in a glass bottle, and the bottle was sealed tightly and stored under the same conditions as in Example 1. Even after 1 week, the coating liquid maintained its fluidity and was usable as a coating liquid.

EXAMPLE 24

A hydrophilic coating composition was produced in substantially the same manner as in Example 23, except that the amount of the hybrid material dispersion AA was changed to 1 part by weight. The coating formation and evaluations were conducted in the same manner as in Example 23. The contact angle of a waterdrop against the surface of the coating was measured and found to be 58°. The waterdrop flowed down swiftly on the coating and there was no residue after the coating was dried. The release of the coating from the substrate was not observed. Further, with respect to the coating, the above-mentioned test for evaluating the stain resistance was conducted for 2 months, and it was found that the stain resistance of the coating was ○. In addition, the coating liquid was stored under the same conditions as in Example 1. Even after the bottle containing the coating liquid had been stored for 1 week or more, the coating liquid maintained its fluidity and was usable as a coating liquid.

EXAMPLE 25

(1) Synthesis of a Hybrid Material

To 1.6 parts by weight of a 5% by weight aqueous solution of polyacrylic acid (reagent manufactured and sold by Polysciences Inc., U.S.A.; weight average molecular weight: 90,000) were added, in this order, 0.7 parts by weight of a 5% by weight aqueous solution of sodium hydroxide and 5 parts by weight of a 10% by weight aqueous solution of sodium metasilicate nonahydrate. The resultant mixture was stirred for 10 minutes, followed by addition of 5 parts by weight of a 9% by weight aqueous solution of strontium nitrate which had separately been prepared to obtain an opaque hybrid material dispersion AB. The hybrid material dispersion AB was subjected to washing operations and drying operations in substantially the same manner as in Example 1 to thereby obtain a final dried hybrid material. The final dried hybrid material was analyzed in the same manner as in Example 23. As a result, it was confirmed that the hybrid material of the present invention was present in the hybrid material dispersion AB. The weight ratio organic domain/inorganic domain was measured and found to be less than 1.0.

(2) Preparation and Evaluation of a Hydrophilic Coating Composition

A hydrophilic coating composition was produced in substantially the same manner as in Example 23, except that the hybrid material dispersion AA was changed to the hybrid material dispersion AB. The coating formation and evaluations were conducted in the same manner as in Example 23. The contact angle of a waterdrop against the surface of the coating was measured and found to be 50°. The waterdrop flowed down swiftly, and there was no residue after the coating was dried. The release of the coating from the substrate was not observed. Further, with respect to the above-mentioned test for evaluating the stain resistance was conducted for 2 months, and it was found that the stain resistance of the coating was ◯. In addition, the coating liquid was stored under the same conditions as in Example 1. Even after the bottle containing the coating liquid had been stored for 1 week or more, the coating liquid maintained its fluidity and was usable as a coating liquid.

EXAMPLE 26

(1) Synthesis of a Water-Soluble Organic Polymer

In a separable flask, 10 parts by weight of 2-acrylamide-2-methylpropanesulfonic acid and 90 parts by weight of purified water were mixed together at 60° C. in a nitrogen atmosphere while stirring. Into the separable flask were charged 10 parts by weight of a 2% by weight aqueous solution of 2,2-azobis(2-(2'-imidazoline-2-yl)propane)-dihydrochloride (VA-044, manufactured and sold by Wako Pure Chemical Industries, Ltd., Japan). The resultant mixture was stirred at 60° C. in a nitrogen atmosphere for 1 hour to obtain poly (2-acrylamide-2-methylpropanesulfonic acid). The weight average molecular weight of the obtained polymer was measured and found to be 800,000.

(2) Synthesis of a Hybrid Material

An opaque hybrid material dispersion AC was produced in substantially the same manner as in Example 25, except that, instead of polyacrylic acid, 2 parts by weight of a 5% (to which diluted) by weight aqueous solution of the above-mentioned (2-acrylamide-2-methylpropanesulfon acid) was used, the amount of a 5% by weight aqueous solution of sodium hydroxied was changed to 0.4 parts by weight, and the amount of strontium nitrate was changed to 3 parts by weight. The hybrid material dispersion AC was subjected to washing operations and drying operations in substantially the same manner as in Example 1 to thereby obtain a final dried hybrid material. The final dried hybrid material was analyzed in the same manner as in Example 23. As a result, it was confirmed that the hybrid material of the present invention was present in the hybrid material dispersion AC. The weight ratio organic domain/inorganic domain was measured and found to be less than 1.0.

(3) Preparation and Evaluation of a Hydrophilic Coating Composition

A hydrophilic coating composition was produced in substantially the same manner as in Example 23, except that the hybrid material dispersion AA was changed to the hybrid material dispersion AC. The coating formation and evaluations were conducted in the same manner as in Example 23. The contact angle of a waterdrop against the surface of the coating was measured and found to be 53°. The waterdrop flowed down swiftly, there was no residue on the coating after the coating was dried. The release of the coating from the substrate was not observed. Further, the coating liquid was stored under the same conditions as in Example 1. Even after the bottle containing the coating liquid had been stored for 1 week or more, the coating liquid maintained its fluidity and was usable as a coating liquid.

EXAMPLE 27

(1) Synthesis of a Hybrid Material

An opaque hybrid material dispersion AD was produced in substantially the same manner as in Example 26, except that, instead of a 10% by weight aqueous solution of sodium metasilicate nonahydrate, a 2.1% by weight colloidal silica (reagent LUDOX SM30, manufactured and sold by Aldrich, Ltd., U.S.A.) was used. The hybrid material dispersion AD was subjected to washing operations and drying operations in substantially the same manner as in Example 1 to thereby obtain a final dried hybrid material. The final dried hybrid material was analyzed in the same manner as in Example 23. As a result, it was confirmed that the hybrid material of the present invention was present in the hybrid material dispersion AD. The weight ratio organic domain/inorganic domain was measured and found to be less than 1.0.

(2) Preparation and Evaluation of a Hydrophilic Coating Composition

A hydrophilic coating composition was produced in substantially the same manner as in Example 23, except that the hybrid material dispersion AA was changed to the hybrid material dispersion AD. The coating formation and evaluations were conducted in the same manner as in Example 23. The contact angle of a waterdrop against the surface of the coating was measured and found to be 53°. The waterdrop flowed down swiftly, there was no residue after the coating was dried. The release of the coating from the substrate was not observed. Further, the coating liquid was stored under the same conditions as in Example 1. Even after the bottle containing the coating liquid had been stored for 1 week or more, the coating liquid maintained its fluidity and was usable as a coating liquid.

EXAMPLE 28

(1) Synthesis of a Hybrid Material

To 5 parts by weight of a 5% by weight aqueous solution of polyacrylic acid (reagent manufactured and sold by Polysciences, Inc., U.S.A.; weight average molecular weight: 90,000) were added, in this order, 2.8 parts by weight of a 5% by weight aqueous solution of sodium hydroxide and 5 parts by weight of a 10% by weight aqueous solution of sodium metasilicate nonahydrate. The resultant mixture was stirred for 10 minutes, followed by addition of 3 parts by weight of a 12.2% by weight aqueous solution of zinc sulfate heptahydrate which had separately been prepared to obtain an opaque hybrid material dispersion AE. The hybrid material dispersion AE was subjected to washing operations and drying operations in substantially the same manner as in Example 1 to thereby obtain a final dried hybrid material. The final dried hybrid material was analyzed in the same manner as in Example 23. As a result, it was confirmed that the hybrid material of the present invention was present in the hybrid material dispersion AE. The weight ratio organic domain/inorganic domain was measured and found to be less than 1.0.

(2) Preparation and Evaluation of a Hydrophilic Coating Composition

A hydrophilic coating composition was produced in substantially the same manner as in Example 24, except that the hybrid material dispersion AA was changed to the hybrid material dispersion AE. The coating formation and evaluations were conducted in the same manner as in Example 23. The contact angle of a waterdrop against the surface of the coating was measured and found to be 60°. The waterdrop flowed down swiftly, there was no residue after the coating was dried. The release of the coating was not observed. Further, the coating liquid was stored under the same conditions as in Example 1. Even after the bottle containing the coating liquid had been stored for 1 week or more, the coating liquid maintained its fluidity and was usable as a coating liquid.

EXAMPLE 29

(1) Synthesis of a Hybrid Material 0.6 Parts by weight of a 20% by weight aqueous solution of polydiallyldimethylammonium chloride (reagent manufactured and sold by Aldrich, Ltd., U.S.A.; weight average molecular weight=100,000 to 200,000) and 5 parts by weight of a 10% by weight aqueous solution of sodium metasilicate nonahydrate were mixed together and the resultant mixture was stirred for 10 minutes. Then, into the mixture were added a mixture of 2.7 parts by weight of a 10.8% by weight aqueous solution of magnesium nitrate hexahydrate and 0.3 parts by weight of a 10% by weight aqueous solution of calcium nitrate tetrahydrate which had separately been prepared to obtain an opaque hybrid material dispersion AF. The hybrid material dispersion AF was subjected to washing operations and drying operations in substantially the same manner as in Example 1 to thereby obtain a final dried hybrid material. The final dried hybrid material was analyzed in the same manner as in Example 3. As a result, it was confirmed that the hybrid material of the present invention was present in the hybrid material dispersion AF. Also, the hybrid material was analyzed by X-ray diffractometry. As a result, a crystalline peak ascribed to magnesium in the inorganic domain was not observed at 2 θ=15° to 55°. Further, the hybrid material was analyzed by $^{29}$SiNMR and it was found that $(Q1+Q2)/(Q3+Q4)=1.9$.

(2) Preparation and Evaluation of a Hydrophilic Coating Composition

A hydrophilic coating composition was produced in substantially the same manner as in Example 9, except that the hybrid material dispersion E was changed to the hybrid material dispersion AF. The coating formation and evaluations were conducted in the same manner as in Example 3. The contact angle of a waterdrop against the surface of the coating was measured and found to be 58°. After a waterdrop flowed on the coating, the release of the coating from the substrate was not observed. Further, with respect to the coating, the above-mentioned test for evaluating the stain resistance was conducted for 2 months, and it was found that the stain resistance of the coating was ⊚. In addition, the coating liquid was stored under the same conditions as in Example 1. Even after the bottle containing the coating liquid had been stored for 1 week or more, the coating liquid maintained its fluidity and was usable as a coating liquid.

EXAMPLE 30

(1) Synthesis of a Hybrid Material 0.6 Parts by weight of a 20% by weight aqueous solution of polydiallyldimethylammonium chloride (reagent manufactured and sold by Aldrich, Ltd., U.S.A.; weight average molecular weight=100,000 to 200,000) and 5 parts by weight of a 10% by weight aqueous solution of sodium metasilicate nonahydrate were mixed together and the resultant mixture was stirred for 10 minutes. Then, into the mixture were charged 3 parts by weight of a 9% by weight aqueous solution of strontium nitrate and 0.33 parts by weight of 1 N hydrochloric acid and the resultant mixture was stirred for 10 minutes. Further, into the mixture was charged 0.21 parts by weight of a polymeric sulfonic acid type surfactant (mighty 150, manufactured and sold by Kao Corporation, Japan) to obtain a light-brown hybrid material dispersion AG. The hybrid material dispersion AG was subjected to washing operations and drying operations in substantially the same manner as in Example 1 to thereby obtain a final dried hybrid material. The final dried hybrid material was analyzed in the same manner as in Example 3. As a result, it was confirmed that the hybrid material of the present invention was present in the hybrid material dispersion AG. Also, the weight ratio organic domain/inorganic domain in the hybrid material in the hybrid material dispersion AG was measured and found to be less than 1.0.

(2) Preparation and Evaluation of a Hydrophilic Coating Composition

A hydrophilic coating composition was produced in substantially the same manner as in Example 9, except that the hybrid material dispersion E was changed to the hybrid material dispersion AG. The coating formation and evaluations were conducted in the same manner as in Example 3. The contact angle of a waterdrop against the surface of the coating was measured and found to be 49°. When the waterdrop was put on the coating, the release of the coating from the substrate was not observed. Further, with respect to the coating, the above-mentioned test for evaluating the stain resistance was conducted for 2 months, and it was found that the stain resistance of the coating was ◯. In addition, the coating liquid was stored under the same conditions as in Example 1. Even after the bottle containing the coating liquid had been stored for 1 week or more, the coating liquid maintained its fluidity and was usable as a coating liquid.

EXAMPLE 31

(1) Synthesis of a Hybrid Material

A light white hybrid material dispersion AH was produced in substantially the same manner as in Example 19, except that, instead of 0.6 parts by weight of a 20% by weight aqueous solution of polydiallyldimethylammonium chloride, 1.2 parts of a 20% by weight aqueous solution of polyvinyl alcohol (GOHSENOL GL-05, manufactured and sold by the Nippon Synthetic Chemical Industry Co., Ltd., Japan) was used and a 4% by weight aqueous solution of sodium hydroxide was not used. The hybrid material dispersion AH was subjected to washing operations and drying operations in substantially the same manner as in Example 1 to thereby obtain a final dried hybrid material. The final dried hybrid material was analyzed in the same manner as in Example 3. As a result, it was confirmed that the hybrid material of the present invention was present in the hybrid material dispersion AH. Also, the hybrid material was analyzed by X-ray diffractometry and it was found that the hybrid material was amorphous at 2 θ=15° to 55°. Further, the weight ratio organic domain/inorganic domain in the hybrid material in the hybrid material dispersion AH was measured and found to be less than 1.0.

(2) Preparation and Evaluation of a Hydrophilic Coating Composition

A hydrophilic coating composition was produced in substantially the same manner as in Example 20, except that the hybrid material dispersion K was changed to the hybrid material dispersion AH. The coating formation and evaluations were conducted in the same manner as in Example 3. The contact angle of a waterdrop against the surface of the coating was measured and found to be 61°. When a waterdrop was put on the coating, the release of the coating from the substrate was not observed. Further, with respect to the coating, the above-mentioned test for evaluating the stain resistance was conducted for 2 months, and it was found that the stain resistance of the coating was ◯. In addition, the coating liquid was stored under the same conditions as in Example 1. Even after the bottle containing the coating liquid had been stored for 1 week or more, the coating liquid maintained its fluidity and was usable as a coating liquid.

EXAMPLE 32

(1) Synthesis of a Hydrophilicity Reagent 14.4 Parts by weight of a 20% by weight aqueous solution of polydiallyldimethylammonium chloride (reagent manufactured and sold by Aldrich, Ltd., U.S.A.; weight average molecular weight=100,000 to 200,000) and 30 parts by weight of a 10% by weight aqueous solution of sodium metasilicate nonahydrate were mixed together and the resultant mixture was stirred for 10 minutes. Then, into the mixture were charged 19.9 parts by weight of a 10.6% by weight aqueous solution of copper sulfate pentahydrate to obtain a blue hybrid material dispersion BA. The hybrid material dispersion BA was subjected to washing operations and drying operations in substantially the same manner as in Example 1 to thereby obtain a final dried hybrid material. The final dried hybrid material was analyzed in the same manner as in Example 3. As a result, it was confirmed that the hybrid material of the present invention was present in the hybrid material dispersion BA. Also, the hybrid material dispersion BA was subjected to a washing operation comprising the above-mentioned washing step 1 using a centrifuge (himac CR20 type, manufactured and sold by Hitachi Koki Co., Ltd., Japan) and the subsequent washing step 2 (which was repeated 4 times total) and a sediment was obtained. The obtained sediment was applied to the surface of a polyethylenetelephthalate film using wire bar #16, followed by drying at 80° C. for 5 minutes to thereby obtain a bluish transparent coating. Both of the coated portion and uncoated portion of the polyethylenetelephthalate film were exposed to steam emitted from a 60° C. hot water bath. As a result, it was found that fogging occurred on the uncoated portion of the film, whereas no fogging was observed on the coated portion of the film.

EXAMPLE 33

A hybrid material dispersion BB was produced in substantially the same manner as in Example 32, except that, instead of a 10.6% by weight aqueous solution of copper sulfate pentahydrate, a 10.8% by weight aqueous solution of magnesium nitrate hexahydrate was used. The hybrid material dispersion BB was subjected to washing operations and drying operations in substantially the same manner as in Example 1 to thereby obtain a final dried hybrid material. The final dried hybrid material was analyzed in the same manner as in Example 32. As a result, it was confirmed that the hybrid material of the present invention was present in the hybrid material dispersion BB. Also, the hybrid material was analyzed by X-ray diffractometry and it was found that the hybrid material was amorphous at 2 θ=15° to 55°. Further, the hybrid material was analyzed by $^{29}$SiNMR and it was found that (Q1+Q2)/(Q3+Q4)=1.2. Also, a coating was formed in the same manner as in Example 32 and the occurrence of fogging by stream was examined. The obtained coating was light white transparent. It was found that this coating was less likely to suffer fogging by the stream than the polyethylenetelephthalate film.

EXAMPLE 34

91 Parts by weight of a 20% by weight aqueous solution of polydiallyldimethylammonium chloride (reagent manufactured and sold by Aldrich, Ltd., U.S.A.; weight average molecular weight=100,000 to 200,000), 14 parts of purified water, 20 parts of sodium metasilicate nonahydrate and 0.8 parts sodium hydroxide were mixed together and the resultant mixture was stirred for 30 minutes. Then, into the mixture was charged 66.5 parts by weight of a 20% by weight aqueous solution of calcium nitrate tetrahydrate to obtain a dispersion. The obtained dispersion was subjected to a washing operation comprising the above-mentioned washing step 1 using a centrifuge (Centra MP 4 type, manufactured and sold by International Equipment Company, U.S.A.) and the subsequent washing step 2 (which was repeated 5 times in total). The resultant material was dried at 60° C. under a reduced pressure of 1 kPa for not less than 8 hr, and then, analyzed by the infra-red spectroscopy. In the analysis, an absorption ascribed to an organic component and an absorption ascribed to a siloxane linkage (a shifted absorption) were observed, respectively, at 2930 cm$^{-1}$ and 970 cm$^{-1}$, thereby confirming the presence of the hybrid material in the obtained hybrid material. The obtained hybrid material which had been washed and dried was used as a sample for the evaluation of the antibacterial property, and mixed with the agar to obtain the above-mentioned test plates (which contain the hybrid material in respective amounts of 4.0 weight/volume %, 2.0 weight/volume %, 1.0 weight/volume % and 0.6 weight/volume %, wherein "volume" means the volume of the agar). As a result of the evaluation, it was found that, in the test plates containing the hybrid material in an amount of 1.0 weight/volume % or more, the growth of bacteria was not observed, which means that the hybrid material had antibacterial property.

EXAMPLE 35

24 Parts by weight of a 20% by weight aqueous solution of polydiallyldimethylammonium chloride (reagent manufactured and sold by Aldrich, Ltd., U.S.A.; weight average molecular weight=100,000 to 200,000), 105 parts of purified water, 20 parts of sodium metasilicate nonahydrate and 0.2 parts sodium hydroxide were mixed together and the resultant mixture was stirred for 30 minutes. Then, into the mixture was charged 40.5 parts by weight of a 20% by weight aqueous solution of zinc sulfate heptahydrate to obtain a dispersion. The obtained dispersion was subjected to a washing and drying operations in the same manner as in Example 34 to obtain a hybrid material, and the obtained hybrid material was analyzed in the same manner as in Example 34. As a result, the presence of the hybrid material in the obtained hybrid material was confirmed. The obtained hybrid material which had been washed and dried was used as a sample for the evaluation of the antibacterial property, and mixed with the agar to obtain the above-mentioned test plates which contain the hybrid material in respective amounts of 4.0 weight/volume %, 2.0 weight/volume %, 1.0 weight/volume % and 0.6 weight/volume % (wherein "volume" means the volume of the agar). As a result of the evaluation, it was found that, even in the test plate containing the hybrid material in an amount of 0.6 weight/volume %, the growth of bacteria was not observed, which means that the hybrid material had antibacterial property.

COMPARATIVE EXAMPLE 1

A coating was formed in substantially the same manner as in Example 1, except that, instead of the hydrophilic coating composition, an acryl latex (E 901, manufactured and sold by Asahi Kasei Kabushiki Kaisha, Japan; solids content: 55% by weight) was used, and the obtained coating was evaluated by the same method as in Example 1. The contact angle of a waterdrop against the surface of the coating was measured and found to be 73°. The waterdrop did not flow down on the coating, and the coating was dotted with residues after the coating was dried. Further, as a result of the evaluation of the stain resistance test for 2 months, it was found that the coating was markedly stained, thereby indicating that the coating had no stain resistance. (As described above, the coating obtained in the Comparative Example 1 is one of the comparative coatings 1 which were used in the tests for evaluating the stain resistance of the coatings obtained in the Examples.)

COMPARATIVE 2

A coating was formed and evaluated in substantially the same manner as in Comparative Example 1, except that the acryl latex was changed to E 316 manufactured and sold by Asahi Kasei Kabushiki Kaisha, Japan (solids content: 45% by weight). The contact angle of a waterdrop against the surface of the coating was measured and found to be 81°. Further, with respect to the coating, the above-mentioned test for evaluation of the stain resistance was conducted for 2 months, and it was found that the coating was markedly stained, thereby indicating that the coating had no stain resistance. (As described above, the coating obtained in Comparative Example 2 is one of the comparative coatings 1 which were used in the tests for evaluating the stain resistance of the coatings obtained in the Examples.)

COMPARATIVE EXAMPLE 3

A white dispersion X was obtained in substantially the same manner as in Example 1, except that polydiallyldimethylammonium chloride (reagent manufactured and sold by Aldrich, Ltd., U.S.A.; weight average molecular weight=100,000 to 200,000) was not used, and a coating composition was produced and evaluated in substantially the same manner as in Example 1, except that, instead of 2 parts by weight of the hydrophilicity reagent, 0.9 parts by weight of the white dispersion X was used. The contact angle of a waterdrop against the surface of the coating was measured and found to be 68°. Further, with respect to the coating, the above-mentioned test for evaluation of the stain resistance was conducted for 2 months, it was found that the coating was markedly stained as in the case of Comparative Example 1, thereby indicating that the coating had no stain resistance.

COMPARATIVE EXAMPLE 4

3 Parts by weight of an acryl latex (E 901, manufactured and sold by Asahi Kasei Kabushiki Kaisha, Japan; solids content: 55% by weight) and 1 part by weight of a 10% by weight aqueous solution of polydiallyldimethylammonium chloride (reagent manufactured and sold by Aldrich, Ltd., U.S.A.; weight average molecular weight=100,000 to 200,000) were mixed together to obtain a coating composition. The obtained coating composition was evaluated in the same manner as in Example 1. The contact angle of a waterdrop against the surface of the coating was found to be 67°. Further, as a result of the evaluation of the stain resistance test for 2 months, it was found that the coating was markedly stained as in the case of Comparative Example 1, thereby indicating that the coating had no stain resistance.

COMPARATIVE EXAMPLE 5

3 Parts by weight of an acryl latex (E 901, manufactured and sold by Asahi Kasei Kabushiki Kaisha, Japan; solids content: 55% by weight) and 2 parts by weight of a 20% by weight aqueous solution of polydiallyldimethylammonium chloride (reagent manufactured and sold by Aldrich, Ltd., U.S.A.; weight average molecular weight=100,000 to 200,000) were mixed together to produce a coating composition. The produced coating composition was evaluated in the same manner as in Example 1. The contact angle of a waterdrop against the surface of the coating was found to be 44°. However, when a waterdrop was put on the coating, the coating itself was dissolved away and the release of the coating from the substrate was observed. Further, when the coating was exposed to the raindrops, the coating was released from the substrate, and hence, the evaluation of the stain resistance could not be conducted.

COMPARATIVE EXAMPLE 6

3 Parts by weight of a 10% by weight aqueous solution of polyacrylic acid (reagent manufactured and sold by Polysciences Inc., U.S.A.; weight average molecular weight: 90,000) and 1.68 parts by weight of a 10% by weight aqueous solution of sodium hydroxide were mixed together to produce an aqueous solution of sodium polyacrylic acid AX. 3 parts by weight of an acryl latex (E 901, manufactured and sold by Asahi Kasei Kabushiki Kaisha, Japan; solids content: 55% by weight) and 1.6 parts by weight of the above-mentioned aqueous solution of sodium polyacrylic acid AX were mixed together to produce a coating composition. The produced coating composition was evaluated in the same manner as in Example 23. The contact angle of a waterdrop against the surface of the coating was found to be 63°. However, when a waterdrop was put on the coating, the coating itself was dissolved away, and the release of the coating from the substrate was observed. Further, when the coating was exposed to the raindrop, the coating was released from the substrate, and hence, the evaluation of the stain resistance could not be conducted.

COMPARATIVE EXAMPLE 7

The production and evaluation of a coating composition were conducted in substantially the same manner as in Example 15, except that an aqueous solution of calcium nitrate tetrahydrate was not used. The contact angle of a waterdrop against the surface of the coating was found to be 80°. Further, with respect to the coating, the above-mentioned test for evaluation of the stain resistance was conducted for 2 months. As a result, it was found that the coating was markedly stained as in the case of Comparative Example 2, thereby indicating that the coating had no stain resistance.

COMPARATIVE EXAMPLE 8

The production and evaluation of a coating composition were conducted in substantially the same manner as in Example 8, except that, instead of the hybrid material dispersion E, 6 parts by weight of a 2% by weight dispersion of a hybrid material (Lucentite SPN, manufactured and sold by CO-OP CHEMICAL CO., LTD., Japan) comprising a quarternary ammonium salt modified by polyoxyalkylene, and a clay, was used. The contact angle of a waterdrop against the surface of the coating was found to be 81°. Also, this clay-containing hybrid material was analyzed by X-ray diffractometry. As a result, a peak having a half width of 6° or less was observed. Further, the hybrid material was analyzed by $^{29}$SiNMR. As a result, only a Q3 peak was observed, and it was found that (Q1+Q2)/(Q3+Q4)=0. Also, with respect to the coating, the above-mentinoed test for the evaluation of the stain resistance was conducted for 2 months. As a result, it was found that the coating was markedly stained as in the case of Comparative Example 2, thereby indicating that the coating had no stain resistance.

COMPARATIVE EXAMPLE 9

15 Parts by weight of a main reagent of an aqueous coating Ceratight Si (manufactured and sold by SK KAKEN Co., Ltd., Japan) containing a white pigment and 1 part by weight of an alkoxide type Ceratight Si curing reagent (manufactured and sold by SK KAKEN Co., Ltd., Japan) were mixed together and the resultant mixture was stirred for 1 hour to obtain a coating composition. Using the obtained coating composition, a coating was formed and evaluated in the same manner as in Example 1. The contact angle of a waterdrop against the surface of the coating was found to be 59°. Further, the coating liquid was stored under the same conditions as in Example 1. 18 Hours after the start of the storage, the coating liquid had lost fluidity and was no longer usable as a coating liquid. (As described above, the coating obtained in Comparative Example 9 is the comparative 2 which was used in the test for evaluating stain resistance of the coatings obtained in the Examples.)

COMPARATIVE EXAMPLE 10

A coating was obtained in substantially the same manner as in Comparative Example 1, except that the polymer emulsion was changed to the polymer emulsion containing a pigment described in Example 20, and the obtained coating was evaluated by the same method as in Comparative Example 1. The contact angle of a waterdrop against the surface of the coating was found to be 87°. Further, with respect to the coating, the above-mentioned test for the evaluation of the stain resistance was conducted for 2 months. As a result, it was found that the coating was markedly stained, thereby indicating that the coating had no stain resistance. (As described above, the coating obtained in Comparative Example 10 is one of the comparative coatings 1 which were used in the tests for evaluating the stain resistance of the coatings obtained in the Examples.)

COMPARATIVE EXAMPLE 11

An inorganic particle dispersion was prepared in substantially the same manner as in Example 34, except that polydiallyldimethylammonium chloride (reagent manufactured and sold by Aldrich, Ltd., U.S.A.; weight average molecular weight=100,000 to 200,000) was not used, and the obtained dispersion was washed and dried by the same method as in Example 34 to obtain a white powder. The obtained powder was used as a sample for the evaluation of the antibacterial property, and mixed with the agar to obtain the above-mentioned test plates which contain the hybrid material in respective amounts of 4.0 weight/volume %, 2.0 weight/volume %, 1.0 weight/volume % and 0.6 weight/volume % (wherein "volume" means the volume of the agar) to evaluate antibacterial property of the above powder. As a result of the evaluation, it was found that, even in the test plate containing the powder in an amount of 4.0 weight/volume %, the growth of bacteria was observed, thereby indicating that that the powder had no antibacterial property.

INDUSTRIAL APPLICABILITY

The hybrid material of the present invention has various functions, so that the hybrid material not only can be used alone as a functional material but also can be used in the form of a dispersion thereof in another organic or inorganic material (matrix). When the hybrid material of the present invention is used as a hydrophilicity reagent and applied to surfaces of various substances, such as a resin surface and a coated surface, it becomes possible to improve the various properties thereof. Specifically, it becomes possible to make it easy to wash away dirt attached to a resin surface or a coated surface with water, to prevent a resin surface or a coated surface from getting tarnished by the adhesion of very small waterdrops, or to prevent a scattering of the light caused by waterdrops on a resin surface or a coated surface. Further, the hydrophilic coating composition using the hybrid material of the present invention is a coating composition which does not require cumbersome operations, such as a double coating operation and a mixing of the liquid components of the coating composition at the time of the use of the coating composition, thus exhibiting excellent workability. The hydrophilic coating formed from the hydrophilic coating composition has excellent properties thus making it easy to wash away dirt attached to the coating; excellent ability to prevent the coating from getting tarnished by the adhesion of waterdrops; and excellent ability to prevent a scattering of the light caused by waterdrops on the coating. When the hybrid material of the present invention is used as an antibacterial/antifungal reagent, the hybrid material exhibits excellent antibacterial/antifungal properties. Especially when the hybrid material is used in the form of a mixture thereof with a cement, the hybrid material exhibits excellent properties. Thus, the hybrid material is a commercially very valuable material.

The invention claimed is:

1. An organic domain/inorganic domain hybrid material comprising:
    an organic domain comprising at least one water-soluble organic polymer having a plurality of functional groups, wherein each functional group is independently selected from the group consisting of an anionic functional group and a cationic functional group, and
    an inorganic domain,
    said organic domain and said inorganic domain being chemically bonded to each other through said functional groups of said organic polymer,
    said inorganic domain comprising a plurality of inorganic bridges having both ends thereof which are, respectively, chemically bonded to said functional groups of said organic polymer, wherein each inorganic bridge is independently represented by the formula (1):

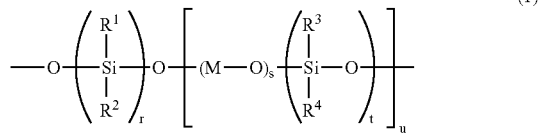

(1)

wherein each M independently represents a divalent metal atom selected from the group consisting of beryllium, magnesium, calcium, strontium, barium, copper, zinc, nickel, iron, manganese, chromium and cobalt, and each of $R^1$ to $R^4$ independently represents a hydrogen atom, a hydroxyl group, a monovalent organic group, a monovalent, siloxane linkage-containing group, or a single bond which is linked to any one of $R^1$ to $R^4$ of an adjacent inorganic bridge through at least an oxygen atom,
        wherein each of r, s and t is independently an integer of 1 or more, and u is an integer of 0 or more, provided that, when both ends of said inorganic bridge are, respectively, bonded to cationic functional groups, u is an integer of 1 or more, and
        wherein, when at least one end of said inorganic bridge is bonded to an anionic functional group, the bonding is made through a divalent metal atom selected from the group consisting of beryllium, magnesium, calcium, strontium, barium, copper, zinc, nickel, iron, manganese, chromium and cobalt,
        wherein, when at least a part of said organic domain is comprised of at least one organic polymer having an anionic functional group and optionally a cationic functional group, the weight ratio of said organic domain to said inorganic domain is less than 1.0, and
        wherein, when at least a part of said organic domain is comprised of at least one organic polymer having an anionic functional group and optionally a cationic functional group, or when said organic domain is comprised of at least one organic polymer having a cationic functional group and having no anionic functional group and when the weight ratio of said organic domain to said inorganic domain is less than 1.0, not all divalent metal atoms of said inorganic domain are simultaneously calcium atoms.

2. The hybrid material according to claim 1, wherein said organic polymer is selected from the group consisting of:
    an organic polymer having a plurality of cationic functional groups,
    an organic polymer having a plurality of anionic functional groups and a plurality of cationic functional groups, and
    a mixture of an organic polymer having a plurality of anionic functional groups and an organic polymer having a plurality of cationic functional groups.

3. The hybrid material according to claim 1, wherein at least a part of the divalent metal atoms of said inorganic domain is comprised of a magnesium atom, and said inorganic domain is amorphous.

4. The hybrid material according to any one of claims 1 to 3, which is produced by a process comprising contacting, in the presence of an aqueous medium and at a pH of 7 or more, the following chemical species (a), (b) and (c) with one another:
    (a) silicate anions formed from a silicate compound or a silicon halide,
    (b) polymer ions formed from at least one water-soluble organic polymer having a plurality of functional groups, wherein each functional group is independently selected from the group consisting of an anionic functional group and a cationic functional group, and
    (c) divalent metal cations formed from a salt of at least one divalent metal selected from the group consisting of beryllium, magnesium, calcium, strontium, barium, copper, zinc, nickel, iron, manganese, chromium and cobalt, provided that, when at least a part of said organic domain is comprised of at least one organic polymer having an anionic functional group and optionally a cationic functional group, or when said organic domain is comprised of at least one organic polymer having a cationic functional group and having no anionic functional group and when the weight ratio of said organic domain to said inorganic domain is less than 1.0, not all divalent metal cations are simultaneously calcium cations.

5. A hydrophilicity reagent comprising an organic domain/inorganic domain hybrid material comprising:
    an organic domain comprising at least one water-soluble organic polymer having a plurality of functional groups, wherein each functional group is independently selected from the group consisting of an anionic functional group and a cationic functional group, and
    an inorganic domain,
    said organic domain and said inorganic domain being chemically bonded to each other through said functional groups of said organic polymer,
    said inorganic domain comprising a plurality of inorganic bridges having both ends thereof which are, respectively, chemically bonded to said functional groups of said organic polymer, wherein each inorganic bridge is independently represented by the formula (1):

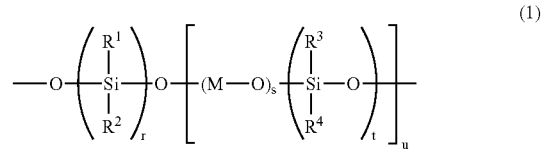

(1)

wherein each M independently represents a divalent metal atom selected from the group consisting of beryllium, magnesium, calcium, strontium, barium, copper, zinc, nickel, iron, manganese, chromium and cobalt, and each of $R^1$ to $R^4$ independently represents a hydrogen atom, a hydroxyl group, a monovalent organic group, a monovalent, siloxane linkage-containing group, or a single bond which is linked to any one of $R^1$ to $R^4$ of an adjacent inorganic bridge through at least an oxygen atom, wherein each of r, s and t is independently an integer of 1 or more, and u is an integer of 0 or more, provided that, when both ends of said inorganic bridge are, respectively, bonded to cationic functional groups, u is an integer of 1 or more, and wherein, when at least one end of said inorganic bridge is bonded to an anionic functional group, the bonding is made through a divalent metal atom selected from the group consisting of beryllium, magnesium, calcium, strontium, barium, copper, zinc, nickel, iron, manganese, chromium and cobalt, wherein, when at least a part of said organic domain is comprised of at least one organic polymer having an anionic functional group and optionally a cationic functional group, the weight ratio of said organic domain to said inorganic domain is less than 1.0.

6. The hydrophilicity reagent according to claim 5, wherein said hybrid material is produced by a process comprising contacting, in the presence of an aqueous medium and at a pH of 7 or more, the following chemical species (a), (b) and (c) with one another:
(a) silicate anions formed from a silicate compound or a silicon halide,
(b) polymer ions formed from at least one water-soluble organic polymer having a plurality of functional groups, wherein each functional group is independently selected from the group consisting of an anionic functional group and a cationic functional group, and
(c) divalent metal cations formed from a salt of at least one divalent metal selected from the group consisting of beryllium, magnesium, calcium, strontium, barium, copper, zinc, nickel, iron, manganese, chromium and cobalt.

7. A hydrophilic coating composition comprising an aqueous dispersion of an organic polymer and, dispersed therein, the hydrophilicity reagent of claim 5 or 6.

8. A hydrophilic coating formed from the hydrophilic coating composition of claim 7.

9. An antibacterial/antifungal reagent comprising an organic domain/inorganic domain hybrid material comprising:
an organic domain comprising at least one water-soluble organic polymer having a plurality of functional groups, wherein each functional group is independently selected from the group consisting of an anionic functional group and a cationic functional group, provided that at least a part of said organic polymer is comprised of at least one organic polymer having a cationic functional group and optionally an anionic functional group, and
an inorganic domain,
said organic domain and said inorganic domain being chemically bonded to each other through said functional groups of said organic polymer,
said inorganic domain comprising a plurality of inorganic bridges having both ends thereof which are, respectively, chemically bonded to said functional groups of said organic polymer, wherein each inorganic bridge is independently represented by the formula (1):

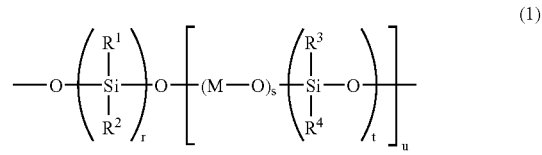

wherein each M independently represents a divalent metal atom selected from the group consisting of beryllium, magnesium, calcium, strontium, barium, copper, zinc, nickel, iron, manganese, chromium and cobalt, and each of $R^1$ to $R^4$ independently represents a hydrogen atom, a hydroxyl group, a monovalent organic group, a monovalent, siloxane linkage-containing group, or a single bond which is linked to any one of $R^1$ to $R^4$ of an adjacent inorganic bridge through at least an oxygen atom, wherein each of r, s and t is independently an integer of 1 or more, and u is an integer of 0 or more, provided that, when both ends of said inorganic bridge are, respectively, bonded to cationic functional groups, u is an integer of 1 or more, and wherein, when at least one end of said inorganic bridge is bonded to an anionic functional group, the bonding is made through a divalent metal atom selected from the group consisting of beryllium, magnesium, calcium, strontium, barium, copper, zinc, nickel, iron, manganese, chromium and cobalt, wherein, when a part of said organic domain is comprised of at least one organic polymer having an anionic functional group and optionally a cationic functional group, the weight ratio of said organic domain to said inorganic domain is less than 1.0.

10. The antibacterial/antifungal reagent according to claim 9, wherein the divalent metal atoms of said inorganic domain are comprised of at least one divalent metal atom selected from the group consisting of copper, zinc, nickel, iron, manganese, chromium and cobalt.

11. The antibacterial/antifungal reagent according to claim 9 or 10, wherein said hybrid material is produced by a process comprising contacting, in the presence of an aqueous medium and at a pH of 7 or more, the following chemical species (a), (b) and (c) with one another:
(a) silicate anions formed from a silicate compound or a silicon halide,
(b) polymer ions formed from at least one water-soluble organic polymer having a plurality of functional groups, wherein each functional group is independently selected from the group consisting of an anionic functional group and a cationic functional group, provided that at least a part of said organic polymer is comprised of at least one organic polymer having a cationic functional group and optionally an anionic functional group, and
(c) divalent metal cations formed from a salt of at least one divalent metal selected from the group consisting of beryllium, magnesium, calcium, strontium, barium, copper, zinc, nickel, iron, manganese, chromium and cobalt.

* * * * *